United States Patent
Thornton et al.

(10) Patent No.: US 7,682,380 B2
(45) Date of Patent: Mar. 23, 2010

(54) KINK-RESISTANT BIFURCATED PROSTHESIS

(75) Inventors: Troy Thornton, San Francisco, CA (US); Randy S. Chan, San Jose, CA (US); Lilip Lau, Sunnyvale, CA (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/184,989

(22) Filed: Jul. 1, 2002

(65) Prior Publication Data

US 2002/0165603 A1 Nov. 7, 2002

Related U.S. Application Data

(63) Continuation of application No. 08/772,372, filed on Dec. 23, 1996, now Pat. No. 6,551,350.

(51) Int. Cl.
*A61F 2/06* (2006.01)
(52) U.S. Cl. ..................... 623/1.13; 623/1.35
(58) Field of Classification Search ............. 623/1.13, 623/1.14, 1.22, 1.35
See application file for complete search history.

(56) References Cited

U.S. PATENT DOCUMENTS

| | | | |
|---|---|---|---|
| 2,638,093 A | 5/1953 | Kulick |
| 3,029,819 A | 4/1962 | Starks |
| 3,096,560 A | 7/1963 | Liebig |
| 3,142,067 A | 7/1964 | Liebig |
| 3,152,618 A | 10/1964 | Rothermal et al. |
| 3,174,851 A | 3/1965 | Buehler et al. |
| 3,351,463 A | 11/1967 | Rozner et al. |
| 3,479,670 A | 11/1969 | Medell |
| 3,514,791 A | 6/1970 | Sparks |
| 3,562,820 A | 2/1971 | Braun |
| 3,625,198 A | 12/1971 | Sparks |
| 3,657,744 A | 4/1972 | Ersek |
| 3,710,777 A | 1/1973 | Sparks |
| 3,753,700 A | 8/1973 | Harrison |
| 3,774,596 A | 11/1973 | Cook |
| 3,805,301 A | 4/1974 | Liebig |

(Continued)

FOREIGN PATENT DOCUMENTS

AU B-42485/89 4/1990

(Continued)

OTHER PUBLICATIONS

Abstract of European Patent EP-0357003 published Mar. 7, 1990.*

(Continued)

*Primary Examiner*—Paul Prebilic
(74) *Attorney, Agent, or Firm*—David J. Johns; Edward I. Amaya

(57) ABSTRACT

The invention consists of an endoluminal prosthesis adapted for placement at a bifurcation site within the body. The stent or stent-graft may be constructed to have segments of differing structural properties. A section of the stent-graft may be constructed to have a single-lumen tubular stent member covering a multilumen graft member. The stent-graft may comprise at least two modular components adapted for in situ assembly. An extended cylindrical interference fit may be used to seal the modular components.

21 Claims, 25 Drawing Sheets

U.S. PATENT DOCUMENTS

| | | |
|---|---|---|
| 3,866,247 A | 2/1975 | Sparks |
| 3,866,609 A | 2/1975 | Sparks |
| 3,868,956 A | 3/1975 | Alfidi et al. |
| 3,927,422 A | 12/1975 | Sawyer |
| 3,938,524 A | 2/1976 | Sparks et al. |
| 3,949,073 A | 4/1976 | Daniels et al. |
| 3,953,566 A | 4/1976 | Gore |
| 3,974,526 A | 8/1976 | Dardik et al. |
| 3,991,767 A * | 11/1976 | Miller et al. .................... 604/8 |
| 3,993,045 A | 11/1976 | Ion |
| 4,011,861 A | 3/1977 | Enger |
| 4,047,252 A | 9/1977 | Liebig et al. |
| 4,112,177 A * | 9/1978 | Salditt et al. ............. 428/315.9 |
| 4,118,806 A | 10/1978 | Porier et al. |
| 4,130,904 A | 12/1978 | Whalen |
| 4,140,126 A | 2/1979 | Choudhury |
| 4,164,045 A | 8/1979 | Bokros et al. |
| 4,187,390 A | 2/1980 | Gore |
| 4,300,244 A | 11/1981 | Bokros |
| 4,306,318 A | 12/1981 | Mano et al. |
| 4,319,363 A | 3/1982 | Ketharanathan |
| 4,355,426 A | 10/1982 | MacGregor |
| 4,411,655 A | 10/1983 | Schreck |
| 4,424,208 A | 1/1984 | Wallace et al. |
| 4,425,908 A | 1/1984 | Simon |
| 4,488,911 A | 12/1984 | Luck et al. |
| 4,494,531 A | 1/1985 | Gianturco |
| 4,501,263 A | 2/1985 | Harbuck |
| 4,502,159 A | 3/1985 | Woodroof et al. |
| 4,503,569 A | 3/1985 | Dotter |
| 4,512,338 A | 4/1985 | Balko et al. |
| 4,517,687 A | 5/1985 | Liebig et al. |
| 4,530,113 A | 7/1985 | Matterson |
| 4,546,500 A | 10/1985 | Bell |
| 4,553,545 A | 11/1985 | Maass et al. |
| 4,557,764 A | 12/1985 | Chu |
| 4,562,596 A | 1/1986 | Kornberg |
| 4,580,568 A | 4/1986 | Gianturco |
| 4,582,640 A | 4/1986 | Smestad et al. |
| 4,592,754 A | 6/1986 | Gupte et al. |
| 4,604,762 A | 8/1986 | Robinson |
| 4,617,932 A | 10/1986 | Kornberg |
| 4,629,458 A | 12/1986 | Pinchuk |
| 4,641,653 A | 2/1987 | Rockey |
| 4,642,117 A | 2/1987 | Nguyen et al. |
| 4,647,416 A | 3/1987 | Seiler et al. |
| 4,649,922 A | 3/1987 | Wiktor |
| 4,655,771 A | 4/1987 | Wallsten |
| 4,665,906 A | 5/1987 | Jervis |
| 4,689,399 A | 8/1987 | Chu |
| 4,728,328 A | 3/1988 | Hughes et al. |
| 4,733,665 A | 3/1988 | Palmaz |
| 4,738,666 A | 4/1988 | Fuqua |
| 4,739,762 A | 4/1988 | Palmaz |
| 4,740,207 A | 4/1988 | Kreamer |
| 4,760,849 A | 8/1988 | Kropf |
| 4,776,337 A | 10/1988 | Palmaz |
| 4,787,899 A | 11/1988 | Lazarus |
| 4,790,313 A | 12/1988 | Borrelly |
| 4,795,458 A | 1/1989 | Regan |
| 4,798,606 A | 1/1989 | Pinchuk |
| 4,800,882 A | 1/1989 | Gianturco |
| 4,816,028 A | 3/1989 | Kapadia et al. |
| 4,816,339 A | 3/1989 | Tu et al. |
| 4,820,298 A | 4/1989 | Leveen et al. |
| 4,830,003 A | 5/1989 | Wolff et al. |
| 4,842,575 A | 6/1989 | Hoffman, Jr. et al. |
| 4,856,516 A | 8/1989 | Hillstead |
| 4,877,025 A | 10/1989 | Hanson |
| 4,878,906 A | 11/1989 | Lindemann et al. |
| 4,886,062 A | 12/1989 | Wiktor |
| 4,886,500 A | 12/1989 | Lazarus |
| 4,892,539 A | 1/1990 | Koch |
| 4,913,141 A | 4/1990 | Hillstead |
| 4,921,479 A | 5/1990 | Grayzel |
| 4,941,870 A | 7/1990 | Okada et al. |
| 4,948,860 A | 8/1990 | Solomon et al. |
| 4,950,227 A | 8/1990 | Savin et al. |
| 4,955,899 A | 9/1990 | Della Corna et al. |
| 4,957,504 A | 9/1990 | Chardack |
| 4,957,508 A | 9/1990 | Kaneko et al. |
| 4,969,458 A | 11/1990 | Wiktor |
| 4,990,151 A | 2/1991 | Wallsten |
| 4,990,155 A | 2/1991 | Wilkoff |
| 4,994,071 A | 2/1991 | MacGregor |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,042,161 A | 8/1991 | Hodge |
| 5,064,435 A | 11/1991 | Porter |
| 5,066,298 A | 11/1991 | Hess |
| 5,067,957 A | 11/1991 | Jervis |
| 5,078,726 A | 1/1992 | Kreamer |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,424 A | 4/1992 | Hoffman, Jr. et al. |
| 5,122,154 A | 6/1992 | Rhodes |
| 5,123,917 A | 6/1992 | Lee |
| 5,127,919 A | 7/1992 | Ibrahim et al. |
| 5,133,732 A | 7/1992 | Wiktor |
| 5,139,480 A | 8/1992 | Hickle et al. |
| 5,147,370 A | 9/1992 | McNamara et al. |
| 5,151,105 A | 9/1992 | Kwan-Gett |
| 5,156,619 A | 10/1992 | Ehrenfeld |
| 5,161,547 A | 11/1992 | Tower |
| 5,162,430 A | 11/1992 | Rhee et al. |
| 5,163,958 A | 11/1992 | Pinchuk |
| 5,171,262 A | 12/1992 | MacGregor |
| 5,178,630 A | 1/1993 | Schmitt |
| 5,192,289 A | 3/1993 | Jessen |
| 5,192,307 A | 3/1993 | Wall |
| 5,195,984 A | 3/1993 | Schatz |
| 5,197,977 A | 3/1993 | Hoffman, Jr. et al. |
| 5,197,978 A | 3/1993 | Hess |
| 5,201,757 A | 4/1993 | Heyn et al. |
| 5,209,735 A | 5/1993 | Lazarus |
| 5,211,658 A | 5/1993 | Clouse |
| 5,213,580 A | 5/1993 | Slepian et al. |
| 5,217,483 A | 6/1993 | Tower |
| 5,221,261 A | 6/1993 | Termin et al. |
| 5,226,913 A | 7/1993 | Pinchuk |
| 5,232,446 A | 8/1993 | Arney |
| 5,236,447 A | 8/1993 | Kubo et al. |
| 5,242,451 A | 9/1993 | Harada et al. |
| 5,246,452 A | 9/1993 | Sinnott |
| 5,258,042 A | 11/1993 | Mehta |
| 5,264,276 A | 11/1993 | McGregor et al. |
| 5,271,410 A | 12/1993 | Wolzinger et al. |
| 5,275,622 A | 1/1994 | Lasarus |
| 5,276,276 A | 1/1994 | Gunn |
| 5,282,824 A | 2/1994 | Gianturco |
| 5,282,846 A | 2/1994 | Schmitt |
| 5,282,847 A | 2/1994 | Trescony et al. |
| 5,282,848 A | 2/1994 | Schmitt |
| 5,282,860 A | 2/1994 | Matsuno et al. |
| 5,290,305 A | 3/1994 | Inoue |

| | | | | | | |
|---|---|---|---|---|---|---|
| 5,306,261 A | 4/1994 | Alliger et al. | | 5,571,169 A | 11/1996 | Plaia et al. |
| 5,306,294 A | 4/1994 | Wnston et al. | | 5,571,172 A | 11/1996 | Chin |
| 5,314,472 A | 5/1994 | Fontaine | | 5,571,173 A | 11/1996 | Parodi |
| 5,324,304 A | 6/1994 | Rasmussen | | 5,571,176 A | 11/1996 | Taheri |
| 5,324,323 A | 6/1994 | Bui | | 5,575,815 A | 11/1996 | Slepian et al. |
| 5,330,528 A | 7/1994 | Lazim | | 5,575,816 A | 11/1996 | Rudnick et al. |
| 5,336,254 A | 8/1994 | Brennen et al. | | 5,575,817 A | 11/1996 | Martin |
| 5,342,348 A | 8/1994 | Kaplan | | 5,578,071 A | 11/1996 | Parodi |
| 5,342,387 A | 8/1994 | Summers | | 5,591,197 A | 1/1997 | Orth et al. |
| 5,344,426 A | 9/1994 | Lau et al. | | 5,591,198 A | 1/1997 | Boyle et al. |
| 5,348,537 A | 9/1994 | Wiesner et al. | | 5,591,228 A | 1/1997 | Edoga |
| 5,354,308 A | 10/1994 | Simon et al. | | 5,591,229 A | 1/1997 | Parodi |
| 5,354,309 A | 10/1994 | Schnepp-Pesch et al. | | 5,593,417 A | 1/1997 | Rhodes |
| 5,356,423 A | 10/1994 | Tihon et al. | | 5,599,305 A | 2/1997 | Hermann et al. |
| 5,360,443 A | 11/1994 | Barone et al. | | 5,607,442 A | 3/1997 | Fischell et al. |
| 5,366,472 A | 11/1994 | Hillstead | | 5,607,444 A | 3/1997 | Lam |
| 5,366,473 A | 11/1994 | Winston et al. | | 5,607,445 A | 3/1997 | Summers |
| 5,366,504 A | 11/1994 | Andersen et al. | | 5,607,468 A * | 3/1997 | Rogers et al. ................ 128/898 |
| 5,370,683 A | 12/1994 | Fontaine | | 5,609,625 A | 3/1997 | Piplani et al. |
| 5,370,691 A | 12/1994 | Samson | | 5,609,627 A | 3/1997 | Goicoechea et al. |
| 5,372,600 A | 12/1994 | Beyar et al. | | 5,609,628 A | 3/1997 | Keranen |
| 5,382,261 A | 1/1995 | Palmaz | | 5,620,763 A | 4/1997 | House et al. |
| 5,383,928 A | 1/1995 | Scott et al. | | 5,622,188 A | 4/1997 | Plaia et al. |
| 5,385,580 A | 1/1995 | Schmitt | | 5,626,561 A | 5/1997 | Butler et al. |
| 5,387,235 A | 2/1995 | Chuter | | 5,628,783 A | 5/1997 | Quiachon et al. |
| 5,389,106 A | 2/1995 | Tower | | 5,628,784 A | 5/1997 | Strecker |
| 5,405,377 A | 4/1995 | Cragg | | 5,628,788 A | 5/1997 | Pinchuk |
| 5,405,378 A | 4/1995 | Strecker | | 5,630,840 A | 5/1997 | Mayer |
| 5,413,598 A | 5/1995 | Moreland | | 5,632,763 A | 5/1997 | Glastra |
| 5,421,955 A | 6/1995 | Lau et al. | | 5,632,772 A | 5/1997 | Alcime et al. |
| 5,423,849 A | 6/1995 | Engelson et al. | | 5,637,113 A | 6/1997 | Tartaglia et al. |
| 5,425,710 A | 6/1995 | Kahir et al. | | 5,639,278 A | 6/1997 | Dereume et al. |
| 5,425,739 A | 6/1995 | Jessen | | 5,643,208 A | 7/1997 | Parodi |
| 5,443,500 A | 8/1995 | Sigwart | | 5,647,380 A | 7/1997 | Campbell et al. |
| 5,449,373 A | 9/1995 | Pinchasik et al. | | 5,649,978 A | 7/1997 | Samson |
| 5,453,084 A | 9/1995 | Moses | | 5,653,743 A | 8/1997 | Martin |
| 5,456,713 A | 10/1995 | Chuter | | 5,653,748 A | 8/1997 | Strecker |
| 5,456,721 A | 10/1995 | Legrand | | 5,662,614 A | 9/1997 | Edoga |
| 5,458,605 A | 10/1995 | Klemm | | 5,662,675 A | 9/1997 | Polanskyj Stockert et al. |
| 5,458,615 A | 10/1995 | Klemm et al. | | 5,662,701 A | 9/1997 | Plaia et al. |
| 5,464,449 A | 11/1995 | Ryan et al. | | 5,662,713 A | 9/1997 | Andersen et al. |
| 5,476,506 A | 12/1995 | Lunn | | 5,665,117 A | 9/1997 | Rhodes |
| 5,480,423 A | 1/1996 | Ravenscroft et al. | | 5,667,523 A | 9/1997 | Bynon et al. |
| 5,484,444 A | 1/1996 | Braunschweiler et al. | | 5,669,924 A | 9/1997 | Shaknovich |
| 5,487,858 A | 1/1996 | Schmitt | | 5,669,930 A | 9/1997 | Igarashi |
| 5,489,295 A | 2/1996 | Piplani et al. | | 5,674,276 A | 10/1997 | Andersen et al. |
| 5,496,364 A | 3/1996 | Schmitt | | 5,676,671 A | 10/1997 | Inoue |
| 5,496,365 A | 3/1996 | Sgro | | 5,676,696 A | 10/1997 | Marcade |
| 5,499,994 A | 3/1996 | Tihon et al. | | 5,676,697 A | 10/1997 | McDonald |
| 5,507,767 A | 4/1996 | Maeda et al. | | 5,681,346 A | 10/1997 | Orth et al. |
| 5,507,769 A | 4/1996 | Marin et al. | | 5,683,449 A | 11/1997 | Marcade |
| 5,507,771 A | 4/1996 | Gianturco | | 5,683,450 A | 11/1997 | Goicoechea et al. |
| 5,509,902 A | 4/1996 | Raulerson | | 5,683,451 A | 11/1997 | Lenker et al. |
| 5,509,931 A | 4/1996 | Schmitt | | 5,683,452 A | 11/1997 | Barone et al. |
| 5,514,154 A | 5/1996 | Lau et al. | | 5,693,084 A | 12/1997 | Chuter |
| 5,522,822 A | 6/1996 | Phelps et al. | | 5,693,085 A | 12/1997 | Buirge et al. |
| 5,522,880 A | 6/1996 | Barone et al. | | 5,693,086 A | 12/1997 | Goicoechea et al. |
| 5,522,881 A | 6/1996 | Lentz | | 5,693,087 A | 12/1997 | Parodi |
| 5,522,961 A | 6/1996 | Leonhardt | | 5,693,088 A * | 12/1997 | Lazarus .................... 623/1.35 |
| 5,540,701 A | 7/1996 | Sharkey et al. | | 5,695,517 A | 12/1997 | Marin et al. |
| 5,540,712 A | 7/1996 | Kleshinkski et al. | | 5,697,970 A | 12/1997 | Schmitt et al. |
| 5,545,210 A | 8/1996 | Hess et al. | | 5,700,285 A | 12/1997 | Myers et al. |
| 5,545,211 A | 8/1996 | An et al. | | 5,700,286 A | 12/1997 | Taraglia |
| 5,549,635 A | 8/1996 | Solar | | 5,709,657 A | 1/1998 | Zimmon |
| 5,549,663 A | 8/1996 | Cottone, Jr. | | 5,713,917 A | 2/1998 | Leonhardt et al. |
| 5,554,180 A | 9/1996 | Turk | | 5,716,365 A | 2/1998 | Goicoechea et al. |
| 5,554,181 A | 9/1996 | Das | | 5,718,724 A | 2/1998 | Goicoechea et al. |
| 5,554,182 A | 9/1996 | Dinh et al. | | 5,718,973 A | 2/1998 | Lewis et al. |
| 5,556,413 A | 9/1996 | Lam | | 5,720,776 A | 2/1998 | Chuter et al. |
| 5,562,724 A | 10/1996 | Vorwerk et al. | | 5,723,003 A | 3/1998 | Winston et al. |
| 5,562,726 A | 10/1996 | Chuter | | 5,723,004 A | 3/1998 | Dereume et al. |
| 5,562,727 A | 10/1996 | Turk et al. | | 5,728,131 A | 3/1998 | Frantzen et al. |
| 5,571,166 A | 11/1996 | Dinh et al. | | 5,728,150 A | 3/1998 | McDonald et al. |

| | | | | | | |
|---|---|---|---|---|---|---|
| 5,730,698 | A | 3/1998 | Fischell et al. | 6,613,072 B2 | 9/2003 | Lau et al. |
| 5,732,572 | A | 3/1998 | Litton | 6,613,077 B2 | 9/2003 | Gilligan et al. |
| 5,735,892 | A | 4/1998 | Myers et al. | 6,673,102 B1 | 1/2004 | Vonesh et al. |
| 5,741,274 | A | 4/1998 | Lenker et al. | 2002/0004676 A1* | 1/2002 | Wallace et al. ............. 623/1.12 |
| 5,741,325 | A | 4/1998 | Chaikof et al. | 2002/0029077 A1 | 3/2002 | Leopold et al. |
| 5,749,825 | A | 5/1998 | Fischell et al. | 2002/0099436 A1 | 7/2002 | Thornton et al. |
| 5,749,880 | A | 5/1998 | Banas et al. | 2002/0156523 A1 | 10/2002 | Lau et al. |
| 5,749,921 | A | 5/1998 | Lenker et al. | 2002/0165603 A1 | 11/2002 | Thornton et al. |
| 5,755,769 | A | 5/1998 | Richard et al. | 2003/0055484 A1 | 3/2003 | Lau et al. |
| 5,769,882 | A | 6/1998 | Fogarty et al. | 2003/0130721 A1 | 7/2003 | Martin et al. |
| 5,776,161 | A | 7/1998 | Globerman | 2003/0208260 A1 | 11/2003 | Lau et al. |
| 5,779,732 | A | 7/1998 | Amundson | | | |
| 5,782,904 | A | 7/1998 | White et al. | FOREIGN PATENT DOCUMENTS | | |
| 5,800,522 | A | 9/1998 | Campbell et al. | AU | B-34742/93 | 1/1993 |
| 5,800,524 | A | 9/1998 | Borghi | AU | B-23795/95 | 10/1995 |
| 5,800,526 | A | 9/1998 | Anderson et al. | AU | 690684 | 4/1998 |
| 5,810,870 | A | 9/1998 | Myers et al. | CA | 2026604 | 4/1991 |
| 5,824,041 | A | 10/1998 | Lenker et al. | CA | 2079417 | 4/1993 |
| 5,840,190 | A | 11/1998 | Scholander et al. | DE | 37 24 514 A1 | 2/1989 |
| 5,843,069 | A | 12/1998 | Butler et al. | DE | 39 18736 A1 | 12/1990 |
| 5,843,158 | A * | 12/1998 | Lenker et al. ............... 623/1.13 | DE | 41 37 857 A1 | 5/1992 |
| 5,843,166 | A | 12/1998 | Lentz et al. | DE | 196 17 823 A1 | 11/1997 |
| 5,843,171 | A | 12/1998 | Campbell et al. | EP | 357003 | 3/1990 |
| 5,865,723 | A | 2/1999 | Love | EP | 0 382 014 A1 | 8/1990 |
| 5,868,704 | A | 2/1999 | Campbell et al. | EP | 0 408 245 A1 | 1/1991 |
| 5,871,537 | A * | 2/1999 | Holman et al. ............. 623/1.23 | EP | 0 418 677 A1 | 3/1991 |
| 5,873,906 | A | 2/1999 | Lau et al. | EP | 0 423 916 B1 | 4/1991 |
| 5,876,432 | A | 3/1999 | Lau et al. | EP | 0 435 518 A1 | 7/1991 |
| 5,888,243 | A | 3/1999 | Silvestrini | EP | 0 312852 | 8/1991 |
| 5,919,225 | A | 7/1999 | Lau et al. | EP | 0 464 755 A1 | 1/1992 |
| 5,925,061 | A | 7/1999 | Ogi et al. | EP | 0 472 731 A1 | 4/1992 |
| 5,925,075 | A | 7/1999 | Myers et al. | EP | 0 540 290 B1 | 5/1993 |
| 5,928,279 | A * | 7/1999 | Shannon et al. ............ 623/1.13 | EP | 0 551 179 A1 | 6/1993 |
| 5,961,546 | A | 10/1999 | Robinson et al. | EP | 0 556 850 A1 | 8/1993 |
| 5,972,441 | A | 10/1999 | Campbell et al. | EP | 0 565 251 A1 | 10/1993 |
| 5,976,650 | A | 11/1999 | Campbell et al. | EP | 0 667 131 A2 | 1/1995 |
| 5,993,489 | A | 11/1999 | Lewis et al. | EP | 0 705577 | 4/1995 |
| 6,001,123 | A | 12/1999 | Lau | EP | 0 689 806 A2 | 5/1995 |
| 6,015,429 | A | 1/2000 | Lau et al. | EP | 0 686 379 A2 | 12/1995 |
| 6,015,430 | A | 1/2000 | Wall | EP | 0 696 447 A2 | 2/1996 |
| 6,015,431 | A | 1/2000 | Thornton et al. | EP | 0 701 800 A1 | 3/1996 |
| 6,017,362 | A | 1/2000 | Lau | EP | 0 696447 | 3/1996 |
| 6,019,787 | A | 2/2000 | Richard et al. | EP | 0 705 577 A1 | 4/1996 |
| 6,019,788 | A | 2/2000 | Butters et al. | EP | 0 716 834 A1 | 6/1996 |
| 6,025,044 | A | 2/2000 | Campbell et al. | EP | 0 747 020 A2 | 12/1996 |
| 6,027,779 | A | 2/2000 | Campbell et al. | FR | 2 678 508 | 8/1993 |
| 6,027,811 | A | 2/2000 | Campbell et al. | GB | 1 506 432 | 4/1978 |
| 6,042,605 | A | 3/2000 | Martin et al. | GB | 1 567 122 | 5/1980 |
| 6,048,484 | A | 4/2000 | House et al. | GB | 1 355 373 | 6/1994 |
| 6,086,604 | A | 7/2000 | Fischell et al. | JP | 49-3634 | 1/1974 |
| 6,098,630 | A | 8/2000 | Papazoglou | JP | 49-3634 | 8/1974 |
| 6,120,477 | A | 9/2000 | Campbell et al. | JP | 49-83634 | 8/1974 |
| 6,139,572 | A | 10/2000 | Campbell et al. | JP | 49083634 | 8/1974 |
| 6,159,565 | A | 12/2000 | Campbell et al. | JP | 02-174859 | 7/1990 |
| 6,165,210 | A | 12/2000 | Lau et al. | JP | 5212121 | 8/1993 |
| 6,193,745 | B1 | 2/2001 | Fogarty et al. | JP | 06-007454 | 1/1994 |
| 6,203,568 | B1 | 3/2001 | Lombardi et al. | JP | 6503734 | 4/1994 |
| 6,254,628 | B1 | 7/2001 | Wallace et al. | JP | 06-181993 | 7/1994 |
| 6,331,188 | B1 | 12/2001 | Lau et al. | JP | 7-500272 T | 1/1995 |
| 6,336,937 | B1 | 1/2002 | Vonesh et al. | JP | 7500272 | 1/1995 |
| 6,352,553 | B1 | 3/2002 | Van der Burg et al. | JP | 07-024688 | 3/1995 |
| 6,352,561 | B1 | 3/2002 | Leopold et al. | JP | 7185011 | 7/1995 |
| 6,357,104 | B1 | 3/2002 | Myers | JP | 08-52165 | 2/1996 |
| 6,361,637 | B2 | 3/2002 | Martin et al. | JP | 8173548 | 7/1996 |
| 6,454,799 | B1 | 9/2002 | Schreck | JP | 8224247 | 9/1996 |
| 6,517,570 | B1 | 2/2003 | Lau et al. | JP | 8224297 | 9/1996 |
| 6,517,571 | B1 | 2/2003 | Brauker et al. | JP | 8-509899 T | 10/1996 |
| 6,520,986 | B2 | 2/2003 | Martin et al. | NL | 1000180 C | 10/1996 |
| 6,547,815 | B2 | 4/2003 | Myers | SU | 1635980 A1 | 12/1988 |
| 6,551,350 | B1 | 4/2003 | Thornton et al. | WO | WO 88/06026 | 8/1988 |
| 6,569,191 | B1 | 5/2003 | Hogan | WO | WO 90/04982 | 5/1990 |
| 6,576,009 | B2 | 6/2003 | Ryan et al. | WO | WO 92/03107 | 3/1992 |
| 6,602,280 | B2 | 8/2003 | Chobotov | | | |

| | | |
|---|---|---|
| WO | WO 92/04097 | 3/1992 |
| WO | WO 92/06734 | 4/1992 |
| WO | WO 92/09246 | 6/1992 |
| WO | WO 93/13825 | 7/1993 |
| WO | WO 9313825 | 7/1993 |
| WO | WO 93/17636 | 9/1993 |
| WO | WO 93/19803 | 10/1993 |
| WO | WO 93/19804 | 10/1993 |
| WO | WO 93/22984 | 11/1993 |
| WO | WO 93/22986 | 11/1993 |
| WO | WO 93/22989 | 11/1993 |
| WO | WO 94/00179 | 1/1994 |
| WO | WO 94/01483 | 1/1994 |
| WO | WO 94/04097 | 3/1994 |
| WO | WO 94/12136 | 6/1994 |
| WO | WO 94/15549 | 7/1994 |
| WO | PCT/US95/01466 | 2/1995 |
| WO | WO 95/05131 | 2/1995 |
| WO | WO 95/05132 | 2/1995 |
| WO | WO 95/09586 | 4/1995 |
| WO | WO 95/21592 | 8/1995 |
| WO | WO 95/26695 | 10/1995 |
| WO | WO 96/10967 | 4/1996 |
| WO | WO 96/18360 | 6/1996 |
| WO | WO 96/18361 | 6/1996 |
| WO | WO 96/21404 | 7/1996 |
| WO | WO 96/24306 | 8/1996 |
| WO | WO-96/24306 A1 | 8/1996 |
| WO | WO 96/35577 | 11/1996 |
| WO | WO 97/21402 | 6/1997 |
| WO | WO 97/21403 | 6/1997 |
| WO | WO 97/21641 | 6/1997 |
| WO | WO 98/30173 | 7/1998 |

OTHER PUBLICATIONS

Blum et al.; "Dacron Endografts for Infrarenal Abdominal Aortic Aneurysms: 2 Year Follow-Up"; Fifth international and Interdisciplinary Symposium on Endoluminal Stents and Grafts (Oct. 10-13, 1996) Washington, D.C., 2 pages total.
U.S. Appl. No. 09/488,229, filed Jan. 20, 2000, Cully et al.
Stedman's Medical Dictionary, (c) 1976, The William and Wilkins Company, 23rd Editional, pp. 694,695.
Dictionary.com at http://dictionary.reference.com/search?q=implantable&r=66 (b).
English language abstract of WO 96/24306.
Wilson et al.; "A Self-Expanding Bifurcated Endovascular Graft for Abdominal Aortic Aneurysm Repair—An Initial Study in a Canine Model";Slide Forum #3—Access And Vascular Prosthesis; pp. M386-M393.
U.S. Appl. No. 09/408,866, filed Sep. 30, 1999, Brenton et al.
U.S. Appl. No. 09/489,604, filed Jan. 20, 2000, Vonesh et al.
U.S. Appl. No. 09/510,937, filed Feb. 22, 2000, Goffena et al.
Blum, U. et al.; "Dacron Endografts for Infrarenal Abdominal Aortic Aneurysms: 2 Year Follow-Up"; Fifth international and Interdisciplinary Symposium on Endoluminal Stents and Grafts (Oct. 10-13, 1996) Washington, D.C., 2 pages total.
Chuter et al.; "Bifurcated stent-grafts for AAA: 3 year follow-up"; Abstracts from the Seventh International Course on Peripheral Vascular Intervention; J. Endovas. Surg. (1996) 3:453.
Chuter et al.; "Bifurcated stent-grafts for AAA: 3 year follow-up"; *Fifth International and Interdisciplinary Symposium on Endoluminal Stents and Grafts* (Oct. 10-13, 1996) Washington, D.C., 2 pages total.
Cragg et al., "Nitinol Intravascular Stent; Results of Preclinical Evaluation", Radiology 189(3): 775-778 (1993).
Cragg, "Percutaneous Femoropopliteal Graft Placement" Radiology 187(3): 643-648 (1993).
Cragg, et al.; "Percutaneous Femoropopliteal Graft Placement" Journal of Vascular and Interventional Radiology 4(4): 455-462 (1993).
Dereume, JP et al.; "Endoluminal Treatment Of Abdominal Aortic Aneurysm with the Corvila Endovascular Graft, Results of a Single-Center, Prospective Feasibility Study of 90 Patients"; *Abstracts from the Seventh International Course on Peripheral Vascular Intervention* J. Endovasc. Surg. (1996) 3:460-461.
Hagen et al., "Self-Expandable Macroporous Nitinol Stents for Transfemoral Exclusion of Aortic Aneurysm in Dogs" Cardiovascular Intervention Radiology 16:339-342 (1993).
Katzen et al., "initial experience performing combined surgical/interventional procedures in the interventional suite" Abstracts from the Seventh International Course on Peripheral Vascular Intervention *J. Endovasc. Surg.* (1996) 3:467.
Laborde et al, "Intraluminal Bypass of Abdominal Aortic Aneurysm Feasibility Study" Radiology 184:185-190 (1992).
Moore et al., "Transfemoral endovascular repair of abdominal aortic aneurysm: Result of the North American EVT phase 1 trial" J. Vasc. Surg. (1996) 23:543-552.
Parodi et al., "long-term follow-up of AAA endoluminal repair" Abstracts from the Seventh International Course on Peripheral Vascular Intervention. J. Endovasc. Surg. (1996) 3:335.
Product Brochure for Catheters, Guidewires, and Stents (no date) Schneider (USA) Inc., Pfizer Hospital Products Group, 5905 Nathan Lane, Minneapolis, Minnesota, 55442.
Product Brochure for Cook-ZTM Stents, Gianturco-Rosch Biliary Design, CookR, A Cook Groups Company, P.O. Box 489, Bloomington, IN, 47402, U.S.A., 4 pages total, (1989).
Product Brochure for PalmazTM Balloon-Expandable Stent, Johnson & Johnson Interventional Systems, 40 Technology Drive, P.O. Box 4917, Warren, NJ, 07059, 2 pages total, (1990).
Product Brochure for the Cragg stent and Cragg EndoPro System 1 MinTecTM Minimally Invasive Technologies , 4 pages total.
White et al., "Endoleak following endoluminal repair of AAA: Diagnosis, significance, and amanagement" Abstracts from the Seventh International Course on Peripheral Vascular Intervention *J. Endovasc. Surg.* (1996) 3:339-340.
World Medical News, World Medical manufacturing Corporation, 13794 NW 4th Street, Bldgs. 210 & 211, Sunrise, Florida, 33325 U.S.A., vol. 5, Issue 3 (Jul. 1996) 3 pages total.
U.S. Appl. No. 08/871,427, filed Jun. 9, 1997, Lau et al., & pending claims as of Apr. 16, 2001.
U.S. Appl. No. 09/207,944, filed Dec. 9, 1998, Vonesh et al., & response dated Aug. 21, 2000.
U.S. Appl. No. 09/235,214, filed Jan. 22, 1999, Brauker et al.
U.S. Appl. No. 09/235,458, filed Jan. 22, 1999, Vonesh et al., & response dated Sep. 28, 2000.
U.S. Appl. No. 09/306,522, filed May 6, 1999, Myers.
U.S. Appl. No. 09/376,931, filed Aug. 13, 1999, Martin et al., & pending claims as of Apr. 16, 2001.

* cited by examiner

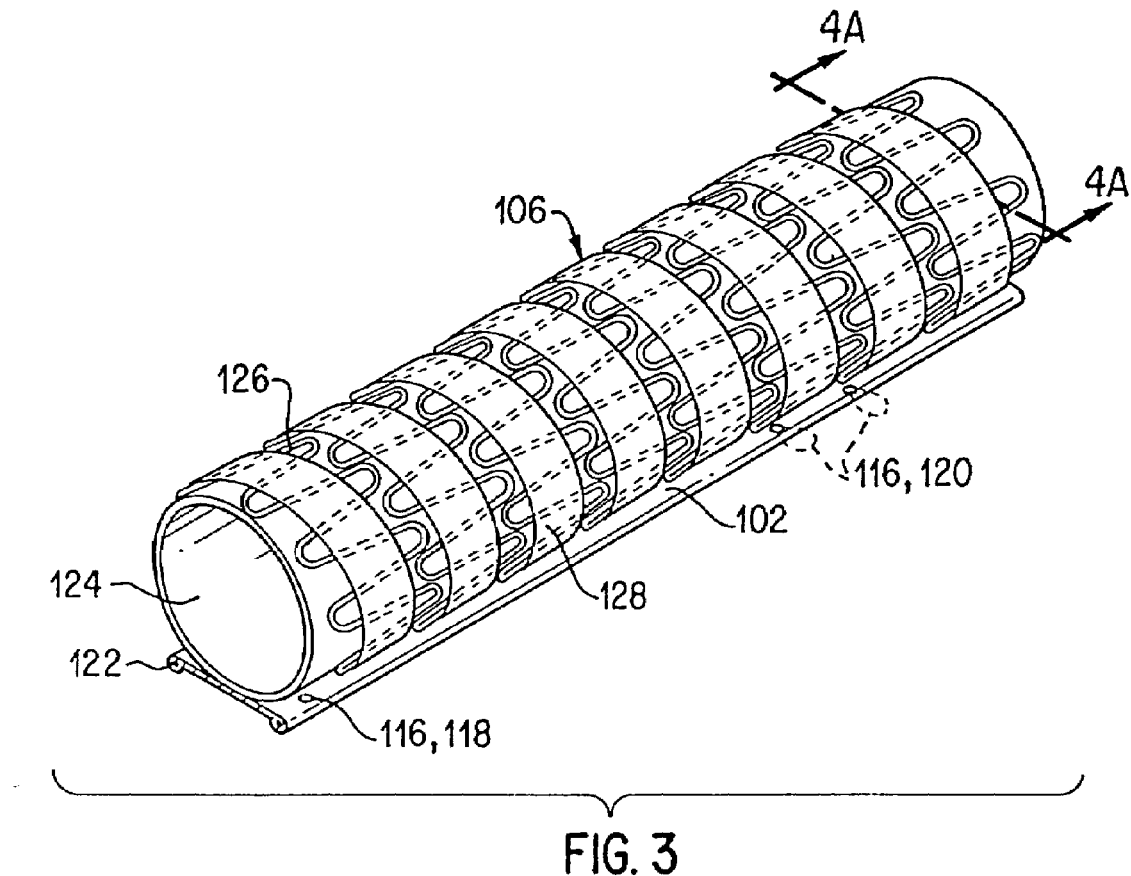
FIG. 3
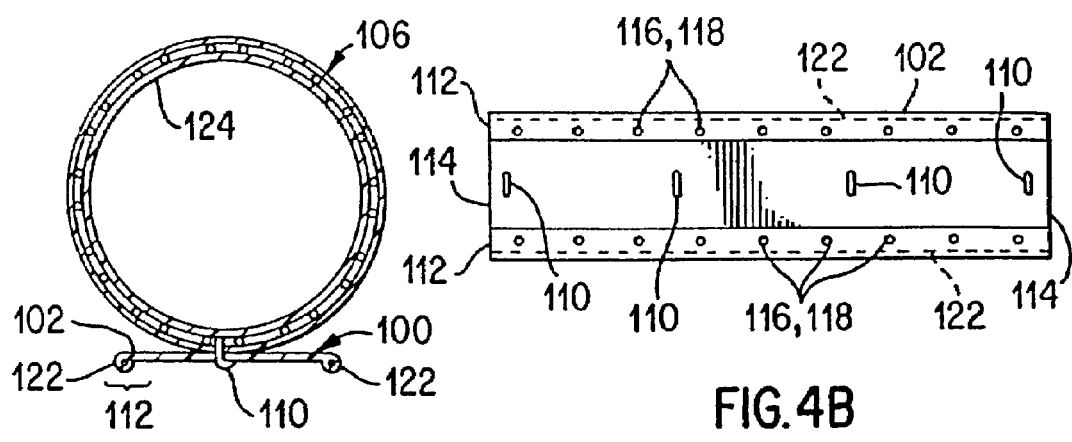
FIG. 4A
FIG. 4B

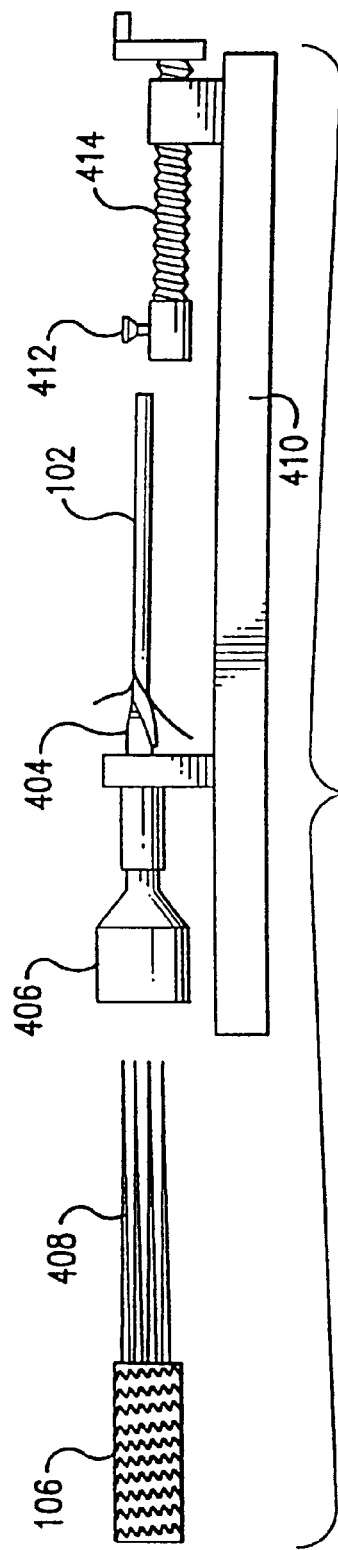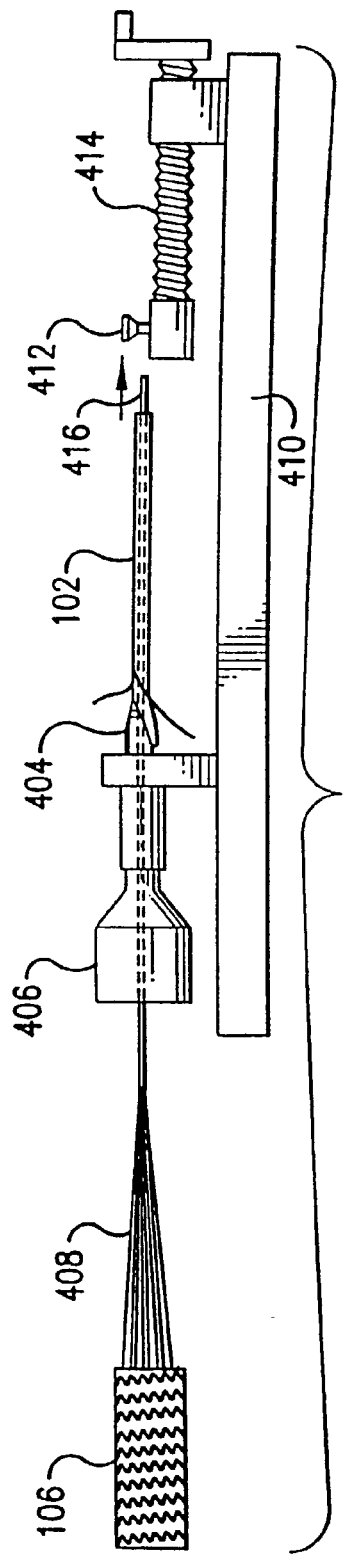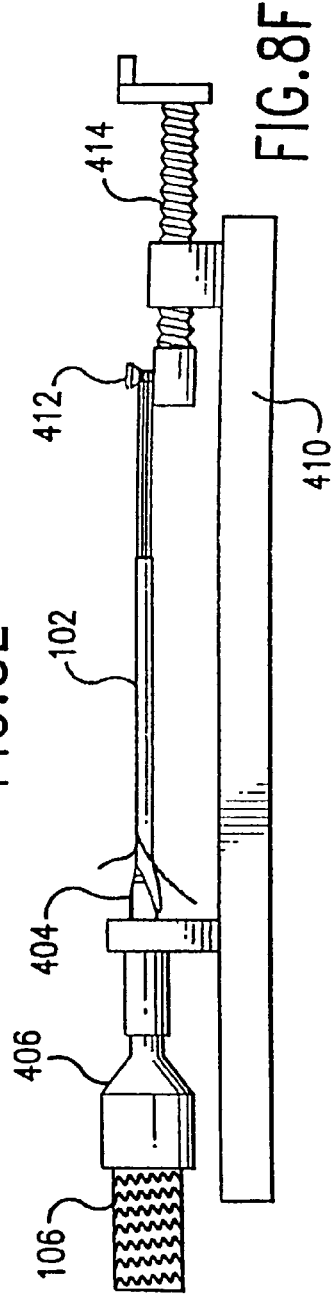

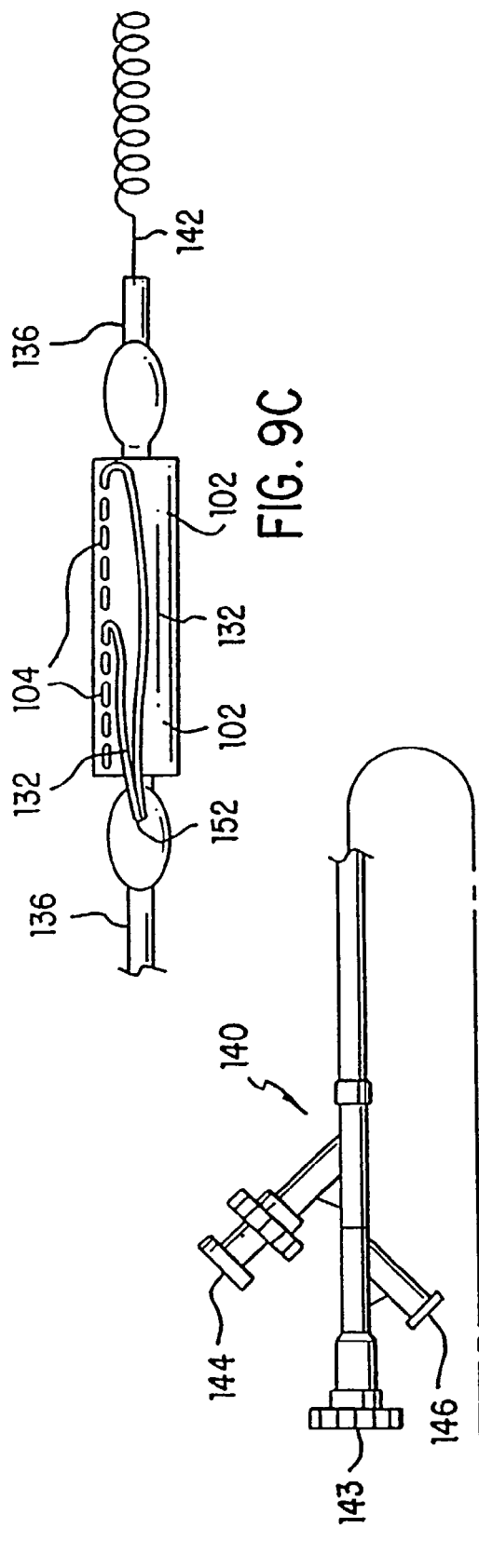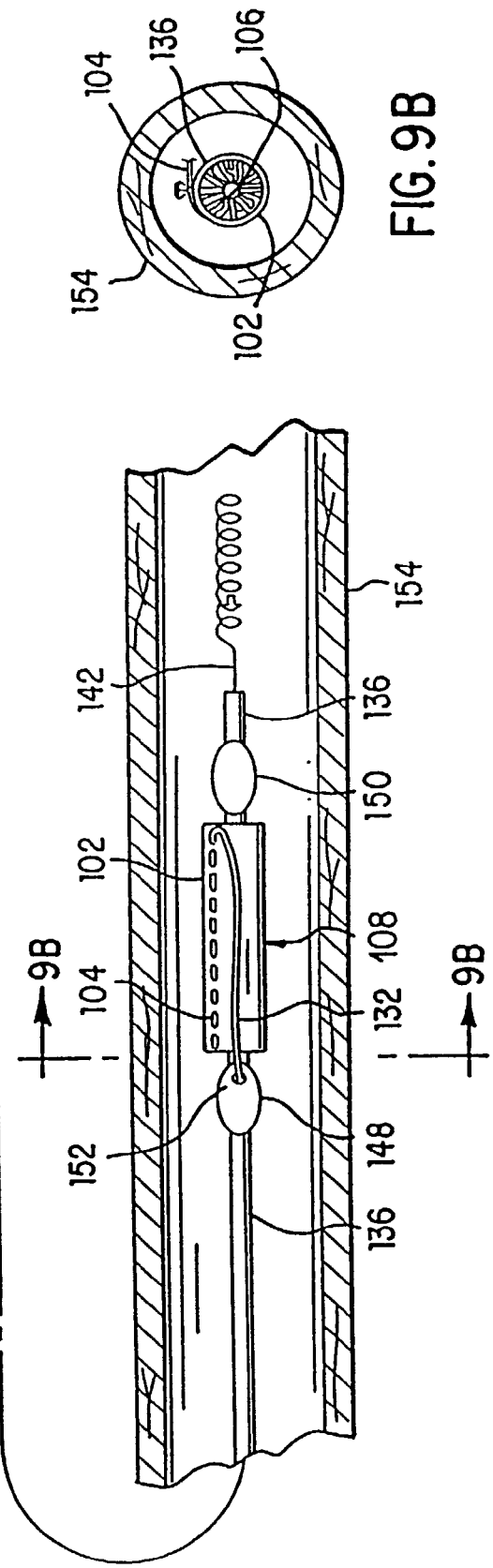

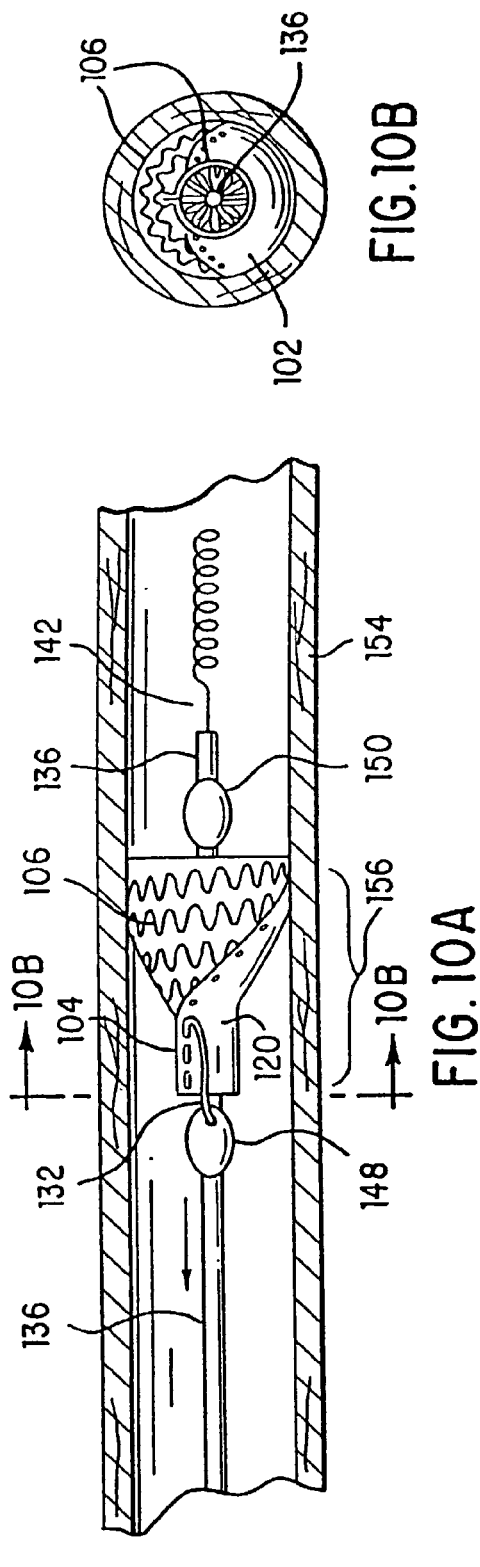
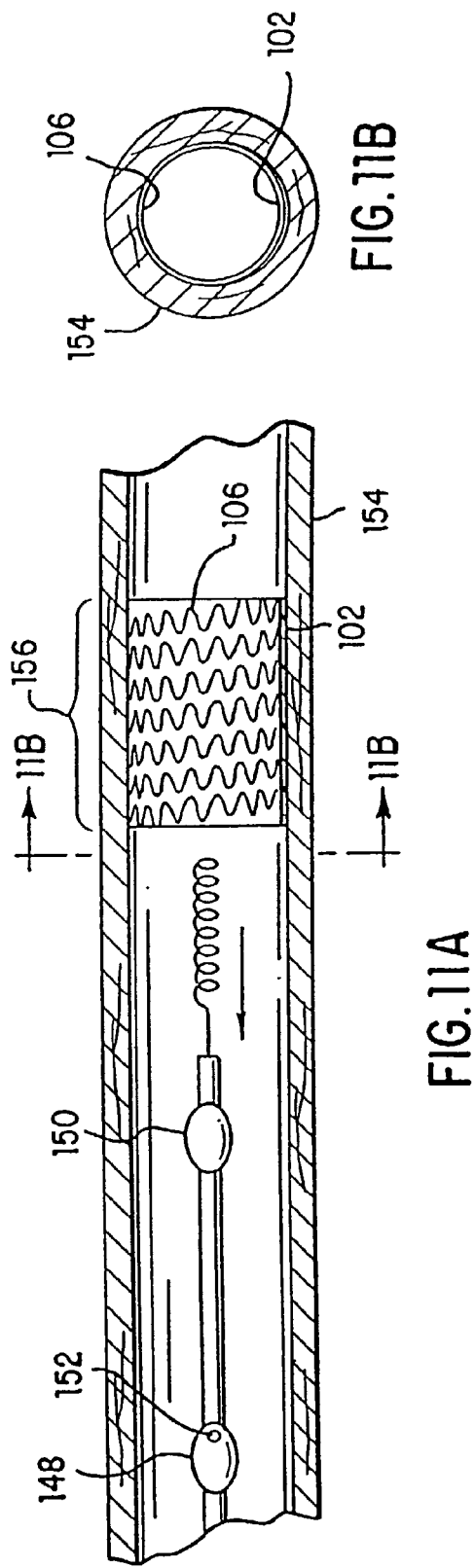

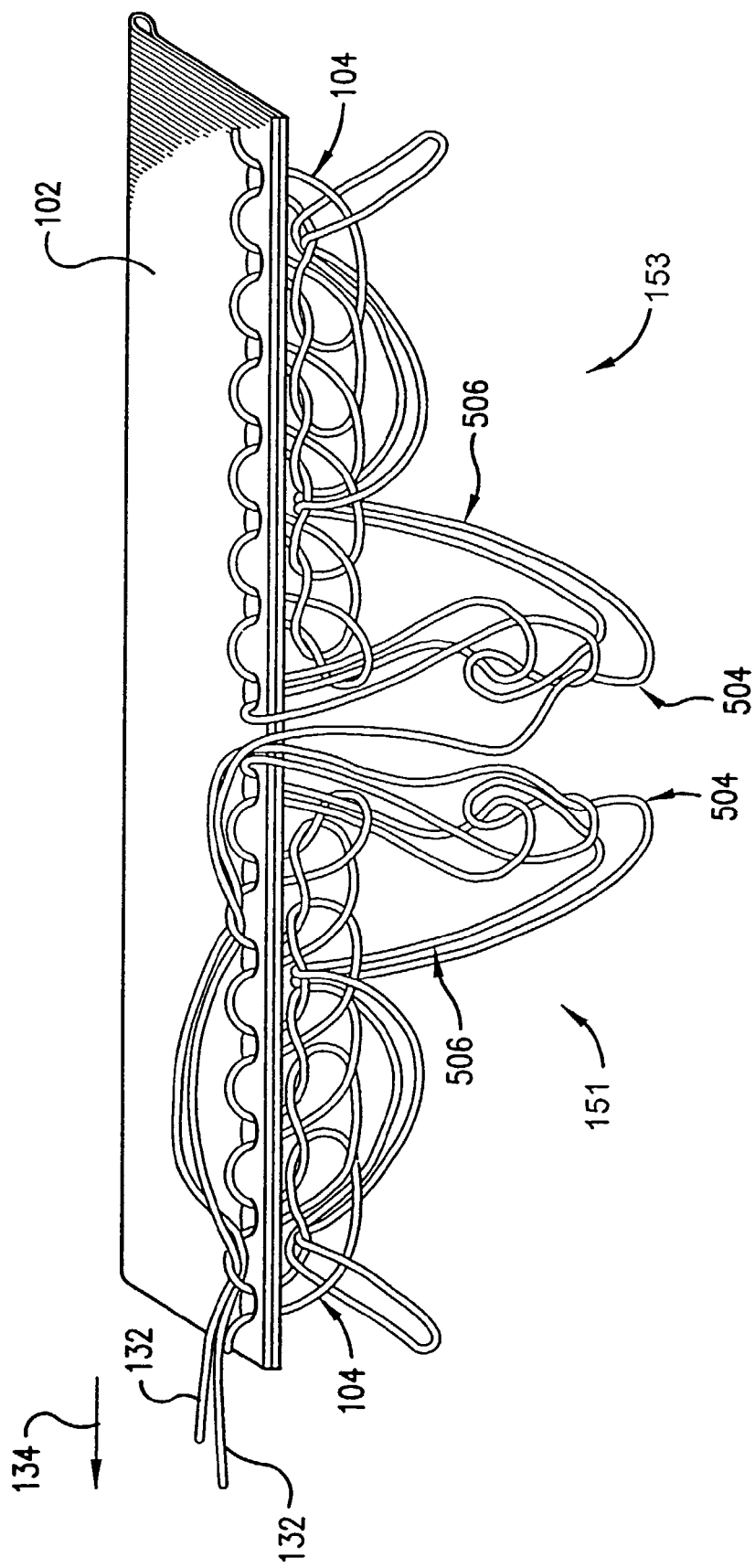

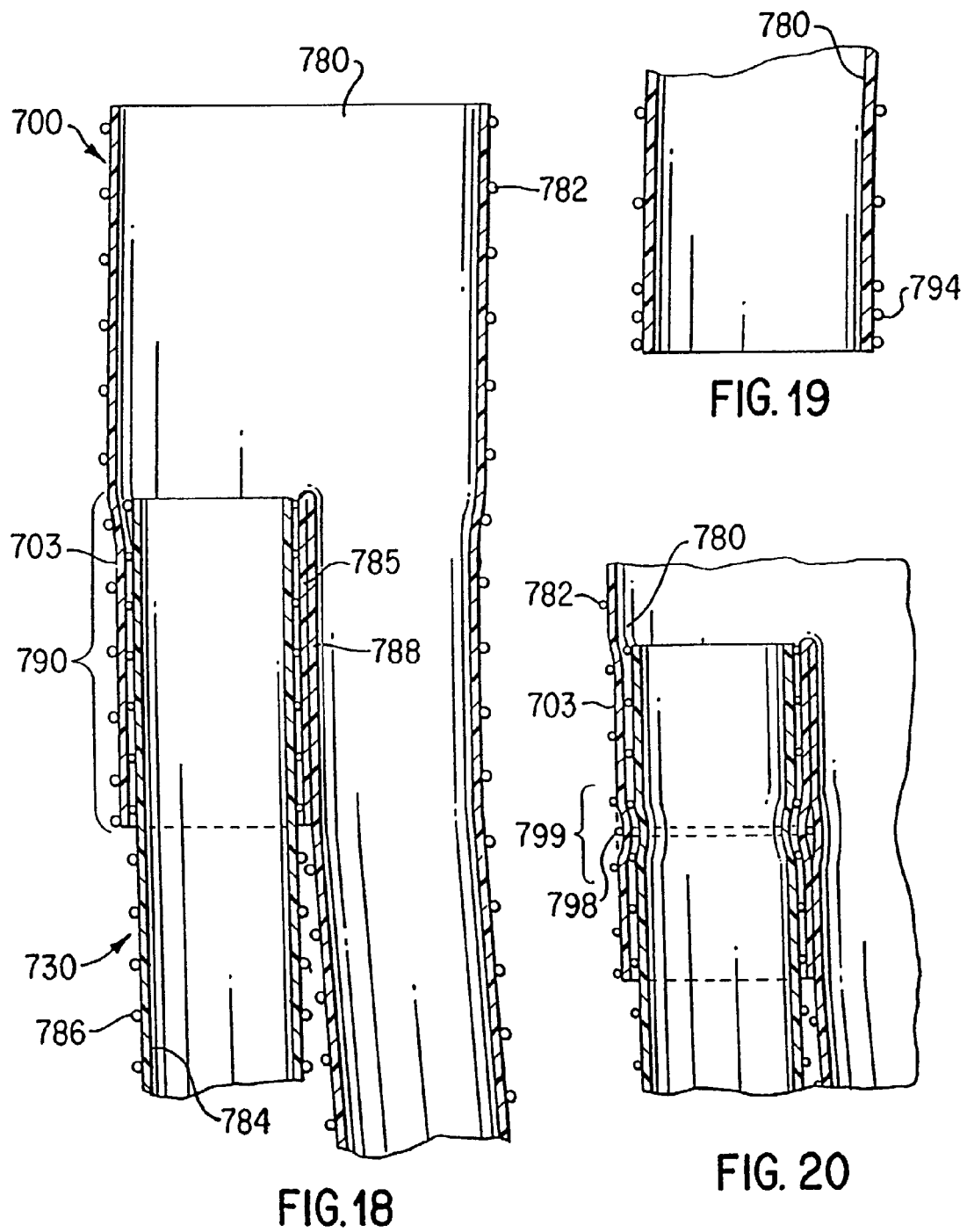

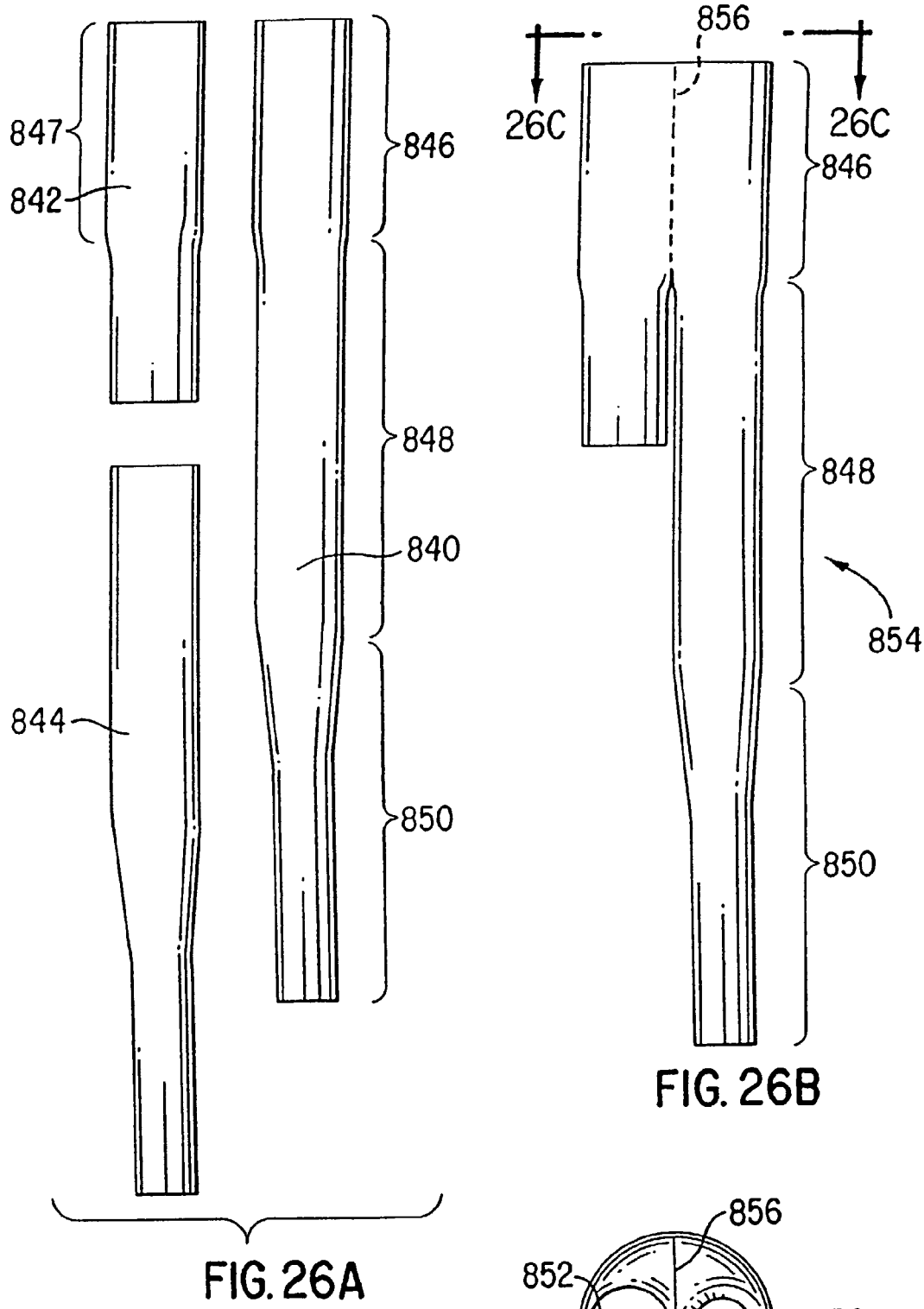
FIG. 26A
FIG. 26B
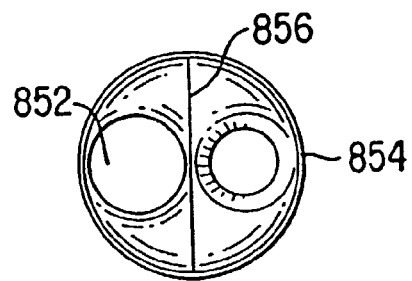
FIG. 26C

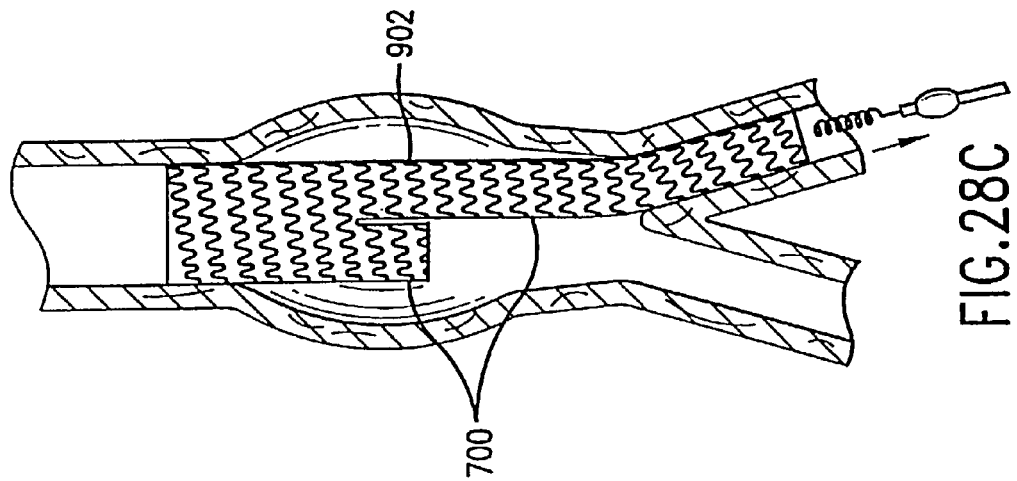
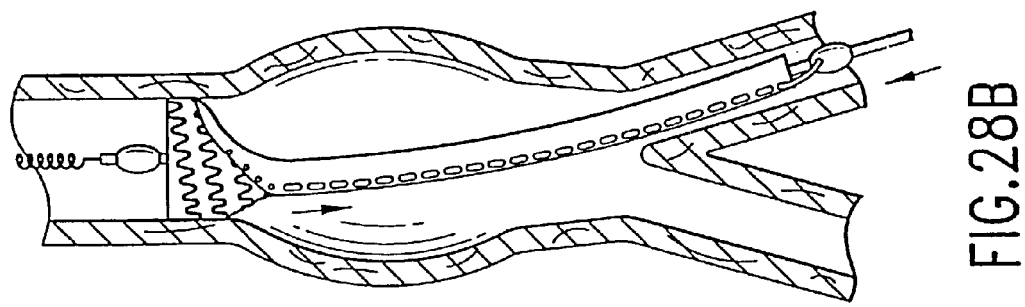
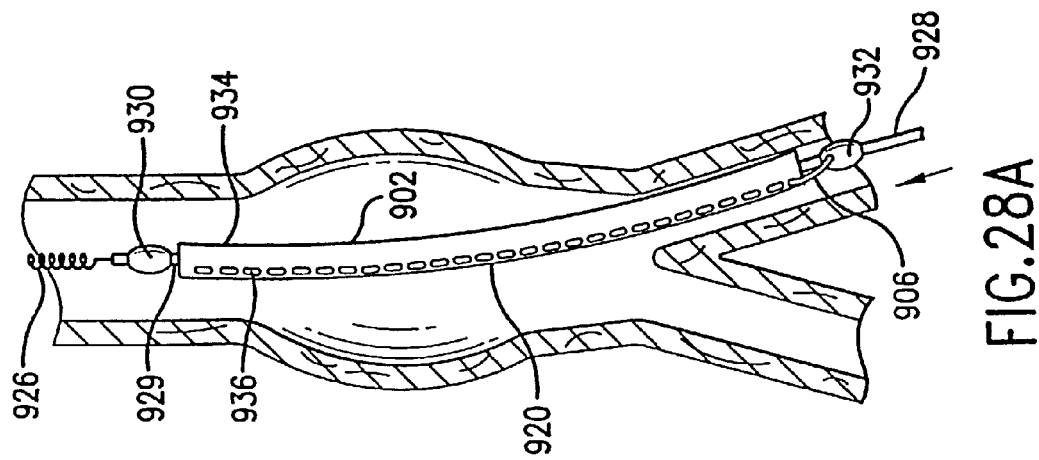

KINK-RESISTANT BIFURCATED PROSTHESIS

This is a continuation application under 37 C.F.R. §1.53(b) of U.S. application Ser. No. 08/772,372, filed Dec. 23, 1996, now U.S. Pat. No. 6,551,350, issued on Apr. 22, 2003, which is incorporated herein by reference in its entirety.

TECHNICAL FIELD

This invention relates generally to implants for repairing ducts and passageways in a body. More specifically this invention relates to an implant adapted for delivery to and repair of a bifurcation site within the body. In one aspect, this invention involves a modular, kink-resistant, bifurcated stent-graft device.

BACKGROUND ART

Treatment or isolation of vascular aneurysms or of vessel walls which have been thickened by disease has traditionally been performed via surgical bypassing with vascular grafts. Shortcomings of this invasive procedure include the morbidity and mortality associated with major surgery, long patient recovery times, and the high incidence of repeat intervention needed due to limitations of the graft or of the procedure.

Minimally invasive alternatives involving stents or stent-grafts are generally known and widely used in certain types of treatments. Intralumenal stents, for example, are particularly useful for treatment of vascular or arterial occlusion or stenosis typically associated with vessels thickened by disease. Intralumenal stents function to mechanically hold these vessels open. In some instances, stents may be used subsequent to or as an adjunct to a balloon angioplasty procedure.

Stent-grafts, which include a graft layer either inside or outside of a stent structure, are particularly useful for the treatment of aneurysms. An aneurysm may be characterized as a sac formed by the dilatation of the wall or an artery, vein, or vessel. Typically the aneurysm is filled with fluid or clotted blood. The stent-graft provides a graft layer to reestablish a flow lumen through the aneurysm as well as a stent structure to support the graft and to resist occlusion or restenosis Treatment of a bifurcation site afflicted with such defects as an occlusion, stenosis, or aneurysm is a particularly demanding application for either stents or stent-grafts. A bifurcation site is generally where a single lumen or artery (often called the trunk) splits into two lumen or arteries (often called branches), such as in a "Y" configuration. For example, one such bifurcation site is found within the human body at the location where the abdominal aortic artery branches into the left and right (or ipsalateral and contralateral) iliac arteries.

When a defect, such as an aneurysm, is located very close to the bifurcation of a trunk lumen into two branch lumens, treatment becomes especially difficult. One reason for this difficulty is because neither the trunk lumen nor either of the branch lumens provides a sufficient portion of healthy, lumen wall on both sides of the defect to which a straight section of single lumen stent or stent-graft can be secured. The stent or stent-graft must span the bifurcation site and yet allow undisturbed flow through each of the branch and trunk lumens.

What is required then is a stent or stent-graft which may be secured to each of the lumen wall a sufficient distance away from the defect and yet is capable of allowing undisturbed flow into each of the branch and trunk lumen. Such a configuration, at least after implantation, generally must have the same Y-shape as described for the bifurcation site. Prior to implantation, the stent or stent-graft may have a Y-shape or may have a modular construction which is assembled into the desired shape as it is implanted.

As we shall see, deployment of implants adapted to meet these needs is also problematic in that they must be deployed and secured in three different lumen which are impossible to access from a single direction. Further, to facilitate intralumenal delivery through a body's tortuous vasculature, the implant must be capable of being compressed into a very small diameter or profile.

Prior devices that deal with treatment at a bifurcation site within the body generally include grafts, stents, and stent-grafts in either a single-piece or modular configuration as described below.

The use of tubular grafts for treating defects at bifurcation sites has been known for some time. Bifurcated grafts have been disclosed, for example, in U.S. Pat. No. 3,029,819 to Starks, U.S. Pat. No. 3,096,560 to Liebig, U.S. Pat. No. 3,142,067 to Liebig, and U.S. Pat. No. 3,805,301 to Liebig. These grafts are typically made of woven fabric or other synthetic material and, because they have no supporting stent structure, typically involve excising the defected segment and suturing the fabric graft in place using common surgical procedures.

A number of bifurcated graft implants have been developed which use some limited means of supporting the one-piece bifurcated graft structure. Typically such means also provide a way to hold the graft open and secure the graft to the lumen wall without the need for sutures so that the graft may be suitable for translumenal delivery via a remote site as opposed to the more invasive surgical grafting techniques as described above.

One such implant is disclosed in U.S. Pat. No. 4,562,596 to Kornberg. Kornberg discloses a bifurcated aortic graft constructed for intraluminal delivery through the femoral artery. The graft consists of a tubular graft material having a plurality of longitudinal supporting struts or stays equipped with hooks or barbs to facilitate attachment within the desired location of the damaged artery. The graft is equipped with a resilient top ring for snugging the upper end of the trunk portion against the aortic wall upon deployment. The graft has a trunk portion and two legs, one of which is shorter than the other. The graft is delivered in a compressed state through a first branch artery with the shorter leg folded against the longer. At some point, as the compressed implant is advance through the first branch artery, the shorter leg clears the bifurcation point and articulates into the luminal region of a second branch artery. The entire implant is then moved in the reverse direction to allow the shorter leg to progress down the second branch. The implant is then expanded to its final shape against the lumen walls by way of a balloon.

Instead of longitudinal struts, other devices have provided the necessary support and securing means for the graft material by employing sections of stent structure at selected locations along the graft. Typically, stent rings may be placed at the trunk and/or branch openings of the stent. Such stent rings are either self-expanding or require balloon expansion.

U.S. Pat. No. 5,489,295 to Piplani et al., for example, discloses a bifurcated graft having a main body and legs formed of a flexible surgically implantable material. Expandable spring attachments are secured to the main body adjacent to the trunk opening and also to one of the legs adjacent to the branch leg opening. Delivered compressed, these expandable spring attachments urge the 25 openings of the graft open upon deployment and serve as anchoring means for securing the graft to the vessel wall. Lumen wall engagement may be enhanced by the addition of barbs or hooks at the apices of the spring attachments.

Another device involving a single-piece bifurcated graft with limited supporting and securing means is disclosed in U.S. Pat. Nos. 5,360,443 and 5,522,880 both to Barone et al. Barone et al. disclose a tubular aortic graft for intraluminal delivery. The graft is secured by the expansion and deformation of a thin-walled tubular member. The thin walled tubular member has a first diameter for delivery. Upon the application of an expanding force from a balloon, the member has a second expanded and deformed diameter for securing the graft to the lumen wall.

As with all such one-piece devices, the delivery of the graft implant is complicated by the fact that each of the trunk and two legs of the graft must be positioned into their respective lumen and then secured into place. This requires the branch legs to be compressed together for delivery through one of the lumen and requires difficult maneuvering of the branch legs to get them unfolded and untwisted into place within their respective branch lumen. This type of delivery requires the graft sections to be highly flexible so that its components may be manipulated as required and requires a larger profile. This demand for high flexibility often results in unsupported graft sections that may be subject to kinking, folding, collapse or the like.

Bifurcated stent devices generally suffer from even greater delivery problems because they are even less compressible and less flexible than their unsupported graft counterparts discussed above. U.S. Pat. No. 4,994,071 to MacGregor, for example, discloses a single-piece bifurcated stent for insertion into a bifurcating vessel. The stent includes a trunk portion constructed from a series of generally parallel loops interconnected by a sequence of half-hitch connections which extend along its length. The parallel loops form a cylindrical lattice which define a flow passageway. Two smaller cylindrical lattices are similarly constructed and attached to the trunk portion to form the branch flow passageways. The stent is designed to be delivered in one piece, over two guidewires (one for each branch) from the direction of the trunk vessel.

Another bifurcated stent example is found in U.S. Pat. No. 5,342,387 to Summers. Summers discloses a Y-shaped bifurcated stent comprising three coil sections (a major coil section and two minor coil sections), constructed of stent wire according to specific coil patterns and joined so as to form an unobstructed support for the trunk and branched vessels. To deploy the bifurcated stent, the stent is compressed around an inflarable bifurcated balloon. The compressed balloon/stent is delivered up one of the branch vessels until one of the minor coils is clear of the bifurcation juncture. Then the stent is backed down, positioning one of the minor coils in each of the branches. The stent is then expanded by the bifurcated "tri-wing" balloon and then the balloon is removed.

To alleviate these complicated delivery problems, some implant devices have used a modular approach. An example of a modular stent may be found in FR 2,678,508 A1. According to that disclosure, in order to provide continuity at junctions, in particular at vessel bifurcations, at least two helicoidal spring elements comprised of self locking coils are used. A first element is constructed to have a first coil diameter section corresponding to the diameter of the aortic artery and a second coil diameter section corresponding to one of the iliac arteries. A second element similarly has two sections, one of which corresponds to the diameter of the second iliac artery, the other equivalent to the diameter of the aortic section of the first element so that the corresponding coils of each element may be delivered separately and locked together in situ.

Another type of modular approach involves using two separate elongated tubes delivered through each of the branch lumen. The tubes, which may consist of a tubular graft element supported by unconnected stent segments, establish the required flow lumen in each of the branch arteries, and in the trunk lumen, are forced together in such a manner as to substantially seal around the periphery. Generally, the shape of the two tubes in the trunk lumen is that of two back-to-back, semi-circular "D" shapes. U.S. Pat. No. 5,507,769 to Marin et al and EP 0 551 179 A1 to Palmaz et al. disclose implants of the type which employ two separate tubes. Palmaz further discloses the use of an expandable tubular member which is secured to the trunk artery prior to delivery of the separate tubes. The purpose of this additional member is help secure the two tubes to the trunk lumen.

Still another type of modular stent-graft device is disclosed in WO 95/21592 (International Application number PCT/US95/01466). In that publication, there is disclosed a modular bifurcated stent or stent-graft comprising two separate modules for delivery in a compressed state and connected together in situ. A first module has a proximal part adapted to engage the trunk artery, then bifurcating into a first distal portion adapted to extend into one branched artery and a female receiving opening to be positioned near the other branched artery. A male proximal portion of a second module is connected to the female receiving opening. According to the disclosure, to ensure the two modules remain connected, it is preferred that the receiving opening has a frustoconical section and the second module has a mating male frustoconical section.

Further related modular stent-graft approaches may be found for example in EP 068 6 379 A2, EP 0 696 447 A2, and U.S. Pat. No. 5,562,724 to Vorwerk et al. While these modular devices tend to offer a measure of improved delivery, continuing problems may include a certain amount of leakage around the openings of the device, leakage at the modular connection, increased compressed profiles, and unoptimal flexibility, kink-resistance, and axial stiffness.

Further it is generally important for any stent or stent-graft to be accurately and quickly deployed so that it may be properly positioned at a desired treatment location. This is especially true with bifurcated devices using a modular approach because, when deployed, the connecting feature must be properly aligned rotationally over a branch artery.

From the foregoing discussion it is evident that it would be desirable to have a self-expanding stent-graft device possessing superior kink-resistance and flexibility to allow the device to follow the natural geometry of the vasculature and, at the same time, allow for sufficient axial stiffness to facilitate accurate placement, resist movement, and prevent leakage. It would be highly desirable to have such a stent or stent-graft device that also provides for a reduced compressed profile for delivery through the body's vasculature. It would be highly desirable for such a stent or stent-graft to have the capability to ensure axial and rotational alignment.

DISCLOSURE OF THE INVENTION

The present invention is an endoluminal prosthesis that avoids the problems and disadvantages of the prior art. The invention generally involves a construction which can be adapted for placement at a bifurcation site within a mammalian body. In one embodiment, the prosthesis is a bifurcated stent or stent-graft.

In another embodiment an inventive stent-graft construction may provide for at least two segments of the stent-graft to have different structural properties from each other. The structural properties may include flexibility and axial stiffness. With such a construction, it is possible to optimize the performance characteristics for ideal delivery and at the same time enhance the device's kink resistance, its ability to maintain its deployed position, and its conformability (which is helpful to effectuate required sealing against the vessel wall). In a preferred embodiment, the axial stiffness is varied according to the presence or absence of extended strut features or the use of a tape member of varying thickness or width.

According to another embodiment of the present invention, the bifurcated stent-graft may be constructed to have a region of single lumen stent covering a multilumen graft. This construction provides for a reduced delivery profile and simplified manufacturing. In one aspect of the present invention, the stent construction is configured to cover a larger portion of periphery of the bifurcated graft.

Another embodiment of the present invention involves a modular stent-graft. A preferred embodiment includes an extended region of cylindrical overlap between the modular components to effectuate improved sealing between the components. In a preferred embodiment the modular components in the area of the cylindrical overlap are constructed to have a diametrical interference fit. In alternate embodiments, sealing is enhanced by the addition of an anchoring ring, a flap of graft material, or both. Certain sealing defects may be further avoided by the use of a scalloping construction graft material around the end openings of the stent-graft.

In yet a further embodiment, the present invention involves a method of forming a bifurcated graft member comprising the steps of heat boding a first tube section to a second tube section such that a common septum is formed and then removing the septum to form a smooth bifurcation.

Another embodiment of the present invention involves a prosthesis anchor for securing the prosthesis to the lumen wall. The anchor may involve a pivotably coupled wire portion extending angularly from the surface of the prosthesis. In one aspect of the inventive anchor, the anchor further has a second wire portion in angular relation to the surface of the prosthesis such that displacement of the second wire toward the surface urges said first wire away from the surface and into the lumen wall.

The above is a brief description of some deficiencies in the prior art and advantages of the present invention. Other features, advantages, and embodiments of the invention will be apparent to those skilled in the art from the following description, accompanying drawings, and appended claims.

BRIEF DESCRIPTION OF THE DRAWINGS

FIG. 3 is a perspective view of the assembly of FIG. 1 with the restraint released and the implant in an expanded state.

FIG. 4A is an end view of the assembly of FIG. 3.

FIG. 4B is a bottom plan view of the restraining member of FIG. 4A.

FIGS. 8A, 8B, 8C, 8D, 8E and 8F diagrammatically show a procedure for loading an expandable stent-graft into a restraining member prior to endolumenal delivery.

FIG. 9A diagrammatically shows delivering a restrained implant to a desired site in a mammalian body lumen with the coupling member configured as shown in FIGS. 7A-7C.

FIG. 9B is a sectional view of FIG. 9A taken along line 9B-9B.

FIG. 9C shows an alternate multiple restraining member arrangement for that shown in FIG. 9A.

FIG. 10A diagrammatically shows partial deployment of the implant assembly illustrated in FIG. 9A showing progressive expansion in a direction away from the distal end of the illustrated guidewire (i.e., toward the illustrated hub).

FIG. 10B is a sectional view of FIG. 10A taken along line 10B-10B.

FIG. 11A diagrammatically shows full deployment of the implant assembly illustrated in FIG. 9A.

FIG. 11B is a sectional view of FIG. 11A taken along 11B-11B.

FIG. 13 illustrates one coupling member configuration for deployment as shown in FIGS. 12A-12D.

FIG. 18 is a cross-sectional view of the stent-graft of FIG. 14B taken along section line 18-18.

FIG. 19 is a cross-sectional view of the stent-graft of FIG. 14A taken along section line 19-19.

FIG. 20 is an enlarged partial cross-sectional view of an alternative contralateral leg connection depicted in FIG. 18 having a localized zone of decreased diameter.

FIG. 26A is a front view of graft components prior to assembly.

FIGS. 26B and 26C are respectively the front view and top view of the assembled graft of FIG. 26A.

FIGS. 28A, 28B, 28C, 28D, and 28E diagrammatically show deployment of a bifurcated stent-graft.

DETAILED DESCRIPTION

Figure 1:
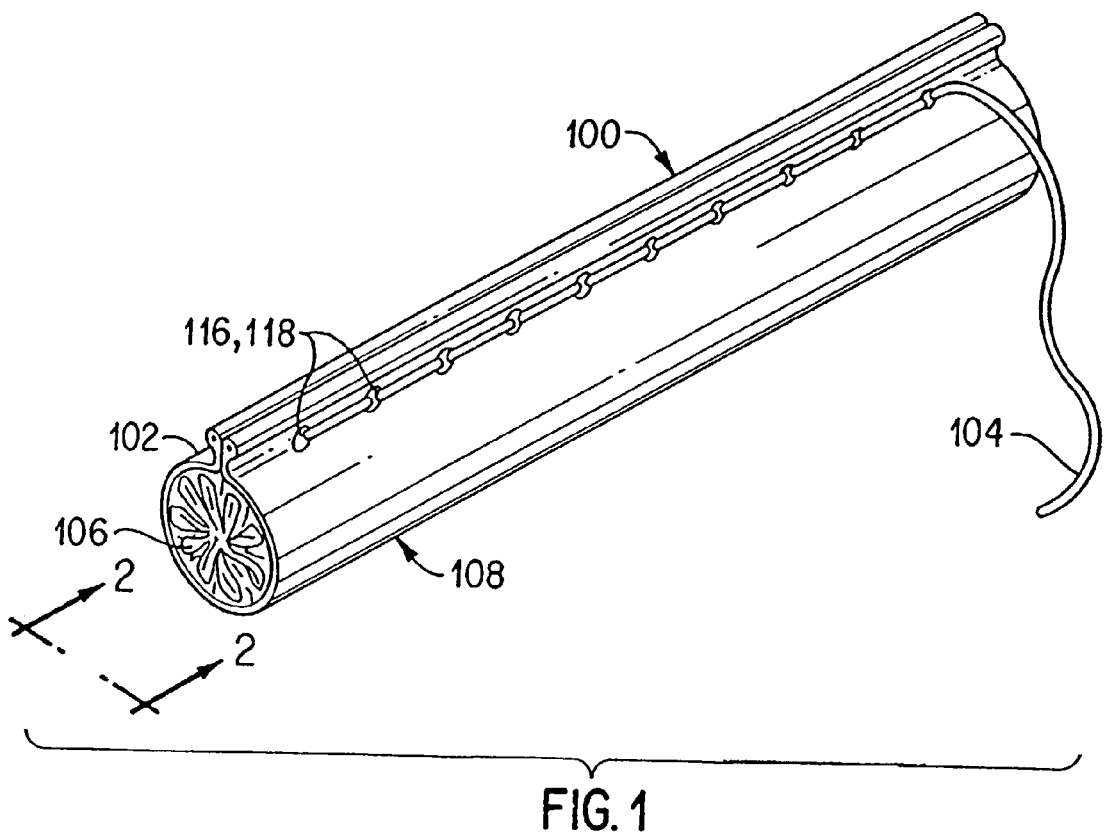
FIG. 1 is a perspective view of a mammalian implant that is restrained in a collapsed state.

The following disclosure relating to the present invention will use certain nomenclature as set forth below. The term distal, as hereinafter used, is meant to refer to locations that are furthest away from the catheter delivery hub. Proximal is meant to refer to locations that are closer to the catheter delivery hub.

Referring to the drawings in detail wherein like numerals indicate like elements, the present invention generally involves bifurcated implants such as stents or stent-grafts for delivery to a desired site through a body's vasculature. This may involve delivery systems that can be used in conjunction with such implants. As this invention is a involves both bifurcated components as well as non-bifurcated components, it is worthwhile to begin by describing in detail the general prosthesis construction and preferred manner of deployment that is applicable to both straight and bifurcated stents or stent-grafts in accordance with FIGS. 1-13. The bifurcated prosthesis will be described with relation to FIGS. 14-28.

Although the invention will be described with reference to the delivery examples illustrated in the drawings, it should be understood that it can be used in conjunction with other delivery devices having constructions different than those shown.

For illustrative purposes, this invention will be described with reference to the location in the human body where the abdominal aorta bifurcates into the left and right (or ipsalateral and contralateral) iliac arteries. It should be understood, however, that the present invention may be used at many other locations within the body.

Referring to FIGS. 1 through 13, delivery systems for delivering implants or devices, such as stents or stent-grafts, to a desired site in mammalian vasculature are shown. Such delivery systems generally include a restraining member that is adapted and configured for surrounding at least a portion of a collapsed or compressed implant and a coupling member(s) for releasably coupling portions of the restraining member to one another to maintain the implant in its collapsed or compressed state.

Figure 2:
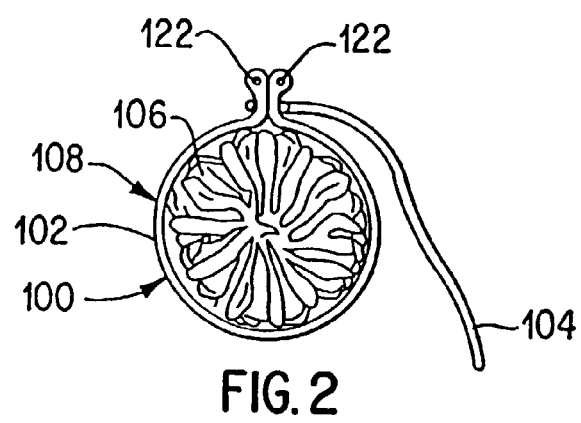
FIG. 2 is an end view of the restrained implant of FIG. 1.

Referring to FIGS. 1-4, an implant delivery system is shown. Delivery system (100), generally includes a restraining member (102), which as shown may be in the form of a sheet of material, and a coupling member (104) for releasably coupling portions of the restraining member to one another. The restraining member portions that are coupled may differ than those illustrated, but preferably are selected to maintain the implant, such as self-expanding stent-graft (106), in a collapsed or compressed state as shown in FIGS. 1 and 2 where the restraining member (102) is shown in the form of a tube. In the illustrative embodiment, the coupling member (104) is shown as a filament or thread-like element which prevents the restraining member (102) from rearranging to a configuration where the stent-graft (106) could expand to its expanded state.

The implant may be collapsed in any suitable manner for placement within the restraining member (102). For example, the implant may be folded or radially crushed before placement within the restraining member (102) as will be described in more detail below. As shown in FIGS. 9-11, a delivery assembly (108), which includes the restraining member (102) and the stent-graft (106), has relatively small cross-sectional dimensions which facilitate endolumenal delivery of the assembly to a site where the natural lumen diameter may be smaller than the expanded diameter of the stent-graft (106).

Referring to FIGS. 3 and 4A, the assembly (108) is shown in a deployed state after removal of the coupling member (104). The restraining member (102) may be fixedly secured to the stent-graft (106) so that the two components remain attached after expansion at the desired deployment site. The attachment between the restraining member and the implant preferably is made to prevent significant movement between the restraining member and stent-graft after deployment which could disrupt endovascular fluid flow. Referring to FIGS. 4A and 4B multiple sutures (110) may be used to fixedly attach the restraining member (102) to the stent-graft (106). More specifically, the sutures can form loops that pass through the restraining member and around portions of the stent as shown in FIG. 4A. It is further noted that although one arrangement of the sutures (110) is shown in FIG. 4B other arrangements may be used.

Although other configurations of the restraining member (102) can be used, a preferred configuration is a generally rectangular one having constant width as shown in FIG. 4B. For example, in the case where the restraining member is used in conjunction with a modular bifurcated stent as will be described below, the restraining member may have a similar rectangular configuration as that shown in FIG. 4B. Alternatively, it may have two differently sized rectangular portions arranged to mate with the regions of different diameter (trunk and leg) or another configuration that would maintain the implant in a collapsed stent when secured. Returning to FIG. 4B, the restraining member may be described as having side margins (112) that extend between the ends (114) of the member. Eyelets (116) are disposed along the side margins so that the coupling member (104) may be laced or threaded therethrough. The eyelets may be in the form of through holes (118), which may be formed by a uniform-diameter puncturing device or by other means such as laser-drilling. Alternatively, the eyelets may be formed by loops (120) which may be attached to the side margins (112) or formed by other means as would be apparent to one of ordinary skill in the art.

It is further desirable to have structural reinforcement at the side margins (112) to minimize or eliminate the possibility of the coupling member (104) from tearing the restraining member (102) when under load. Reinforced side margins may be formed by folding a portion of the restraining member (102) over a reinforcement member (122), such as a small diameter suture, which may be heat bonded between the two layers of sheet material. With this construction, a relatively low profile bead of material along the side margins (112) prevents or minimizes the possibility of tear propagation and, thus, accidental uncoupling of the restraining member (102). The small diameter suture (122) may comprise ePTFE, for example.

As the restraining member (102) constrains a collapsed self-expanding stent-graft, for example, forces resulting from stored spring energy in the collapsed stent-graft (106) will be acting on the restraining member (102) when it is configured for delivery. Thus, the restraining member (102) may comprise a material which is creep resistant and can withstand required loads without stretching over time. The restraining member (102) may comprise, for example, ePTFE, which is believed to provide suitable creep resistance, flexibility, and biocompatibility in a thin sheet form which can be heat bonded. Other materials also may be used including polyethers such as polyethylene terepthalate (DACRON® or MYLAR®) or polyaramids such as KEVLAR®.

The thread-like coupling member (104) may also comprise ePTFE. Sutures of polyethers such as polyethylene terephalate (DACRON® or MYLAR®) or polyaramids such as KEVLAR® or metal wire comprising nitinol, stainless steel or gold may also be used for the coupling member (104). The coupling member (104) may simply extend to form a remote pull line as will be discussed below. Alternatively, a metallic pull line, such as one comprising stainless steel may be coupled to a nonmetallic coupling member (104) such as one comprising ePTFE. The coupling may be made by folding the end of the metallic pull line back upon itself to form an eyelet and threading the coupling member therethrough and securing it to the eyelet with a knot.

It is further noted that the width of the restraining member, when in a flat orientation as shown in FIG. 4A, preferably is less than the diameter of the implant. Typically the restraining member width will be less than about 40 mm (typically about 25-40 mm when the device is sized for thoracic aorta applications), and typically less than about 15 mm in other applications where the lumen is smaller. The sheet of material preferably has a thickness less than 0.010 inch (0.254 mm) and more preferably less than 0.005 inch (0.127 mm). In addition, the length of the restraining member preferably is less than or equal to that of the implant.

Additionally, a retraction assembly may be provided to retract the restraining member during expansion of the implant, so that the length of the restraining member is maintained to be about equal to or less than that of the implant. The expandable portion of the implant may undergo minor amounts of shortening along the axial direction due to the expansion thereof in the radial direction, which may lead to an overlap of the restraining member at the ends of the implant, but for the use of some type of retraction assembly in these situations. The retraction assembly minimizes or eliminates the risk of the restraining member extending beyond the implant and interfering with any channel formed by the implant, or any fluid flowing therethrough after expansion.

Figures 5A, 5B:
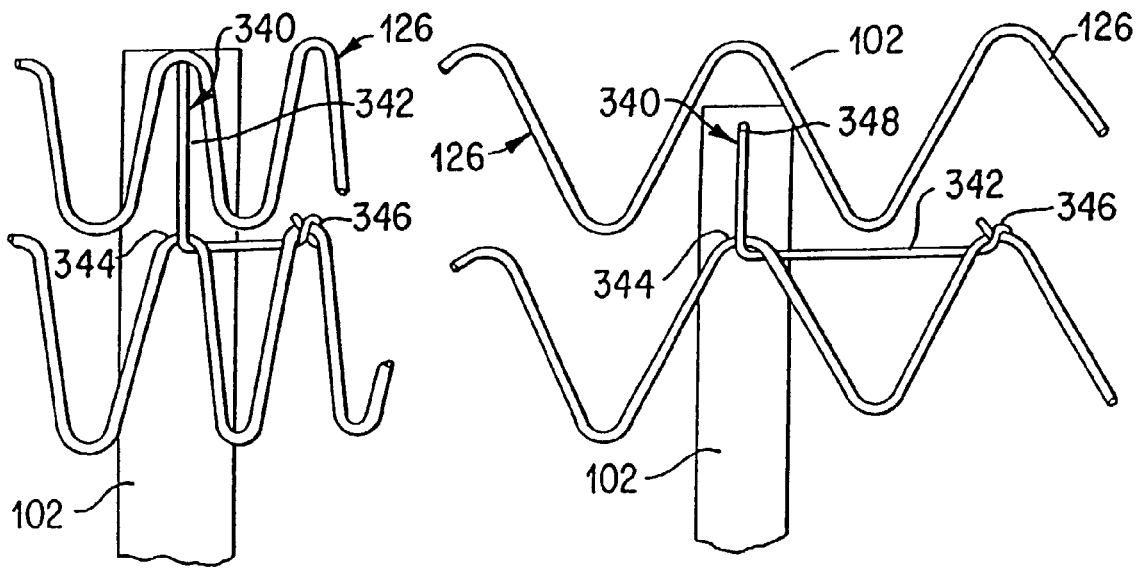
FIG. 5A shows a restraining member retraction mechanism where the mechanism is in an unactuated state.
FIG. 5B shows the mechanism of FIG. 5A in an actuated state.

Referring to FIGS. 5A-5D, retraction assemblies or mechanisms are shown. In FIG. 5A, a retraction assembly (340) is shown including a biocompatible filament (342), which includes a portion that is stitched, tied or otherwise fixed to the restraining member (102), as shown at an attachment point (348), adjacent to one end of the restraining member. Filament (342) is passed underneath the members forming the first or end helical turn of the stent (126) and looped under or otherwise slidably secured to a portion of the second, third or another helical turn other than the first helical turn such a an apex or bend portion (344) in a second turn. The other end portion of filament (342) is further fixed, by tying or other means, to a portion of the stent that is circumferentially spaced from the attachment point (348) or the apex or bend portion (344), for example, such as an apex or bend portion (346) of the same helical turn. Preferably, the filament (342) is looped through an apex portion (344) of the second helical turn and tied to an apex portion (346) which is adjacent to the apex portion (344) as shown in FIG. 5A.

FIG. 5A shows the stent in the compressed state. Upon expansion of the stent, as mentioned above, the members of the stent expand to effect the radial expansion of the stent, as shown in FIG. 5B. Because the distance between apex portions (344) and (346) becomes greater upon expansion of the stent, and because the filament (342) is relatively unyielding and inelastic, the distance between the attachment point (348) and the apex portion (344) necessarily decreases. The result is that the end of the restraining member (102) is retracted with respect to the stent (126), as shown in FIG. 5B. Thus, the retraction along the longitudinal axis of the restraining member is driven by the expanding distance between adjacent apexes of the stent (126) in this embodiment. Although only one retraction mechanism is shown at one end of the restraining member, another similarly configured and arranged retraction mechanism may be used at the other end of the restraining member.

Figures 5C, 5D:
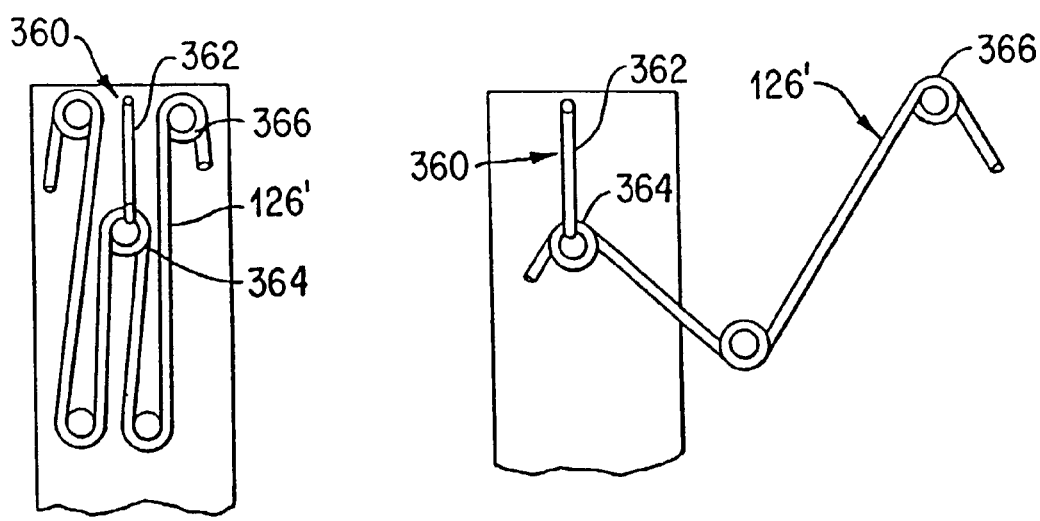
FIG. 5C shows an alternate construction of a retraining member retraction mechanism where the mechanism is in an unactuated state.
FIG. 5D shows the mechanism of FIG. 5C in an actuated state.

FIGS. 5C and 5D show another embodiment for a retraction assembly. The views of this assembly (as are those shown in FIGS. 5A and 5B) are taken from a location between the generally cylindrical graft and stent looking radially outward. In contrast to that shown above where one end portion of a filament is secured to the restraining member and another to a portion of the stent that circumferentially moves during stent expansion, the other end of the filament is secured to a portion of a stent that moves generally parallel to the longitudinal axis of the stent (axially) as the stent expands. In this embodiment, at least one apex portion (364) of an end helix of the stent member (126') (which differs from stent (126) in that it includes eyelets or loops which may be formed as shown in the drawings) is made shorter than the majority of apex portions (366). However, the apex portions may be otherwise configured such as those shown in FIGS. 4A and 4B. A filament (362) is tied or otherwise fixed at one end to apex portion (364), and at the other end, to one end portion of the restraining member (102). As shown in FIG. 5D, upon radial expansion of the stent, inwardly positioned apex portion (364) retracts to a greater extent in the longitudinal or axial direction than the full height apex portions (366) which are shown in the last or most outwardly positioned turn of the stent. This relative greater retraction directly translates through filament (362) such that the end of the restraining member (102) is retracted relative to apex portions (366). As described above, another similarly constructed retraction mechanism may be provided at the other end of the restraining member.

Returning to FIG. 3, one stent-graft construction that may be used in conjunction with the delivery systems disclosed herein is shown. Stent-graft (106) generally includes a thin-walled tube or graft member (124), a stent member (126), which can be a self-expanding stent, and a ribbon or tape member (128) for coupling the stent (126) and graft (124) members together. The stent (126) and graft (124) members may be heat bonded together, thus sealing in portions of the stent member (126) that are between the tape member (128) and the graft member (124). The mechanical properties of the stent-graft (106) may be customized, for example, through materials selection, by varying the structural pattern of the stent member, varying the thickness of the tape (128) and graft (124) members, and varying the pattern with which the tape member contacts the stent and graft members.

As shown in FIG. 1A, the tape member (128) may cover only a portion of the stent member (126) as it follows the helical turns of the undulating stent member. With this construction, regions of the stent member do not interface with the tape member when the stent-graft is in an uncompressed state, for example. This is believed to advantageously reduce shear stresses between the stent member (126) and the tape member (128) when the stent-graft undergoes bending or compression, thereby reducing the risk of tearing the graft (124) or tape (128) members or causing delamination between the stent (126) and graft (124) members.

The tape member (128) also preferably has a generally broad or flat surface for interfacing with the stent (126) and graft (124) members as compared to filament or thread-like structures such as sutures. This increases potential bonding surface area between the tape member (128) and the graft member (124) to enhance the structural integrity of the stent-graft. The increased bonding surface area also facilitates minimizing the thickness of the tape member (128). It has been found that a tape member in the form of a generally flat ribbon as shown in the drawings provides desired results.

Tape members having widths of 0.025, 0.050 and 0.075 inches applied to a stent member having a peak-to-peak undulation amplitude of about 0.075 inch are believed to provide suitable results. However, it has been found that as the tape member band width increases, the stent-graft flexibility generally is diminished. It is believed that a tape member width of about one-fourth to three-fourths the amplitude of the stent member undulations, measured peak-to-peak, may be preferred (may be more preferably about one-third to two-thirds that amplitude) to optimize flexibility. It also has been found that by positioning one of the lateral margins of the tape member adjacent to the apexes, the tape member width may be reduced without significantly sacrificing apex securement. Varying the width of the tape member (e.g., varying width of the tape along the length of the stent graft) can also result in the adjustment of other structural properties. Increasing the width can also potentially increase the radial stiffness and the burst pressure and decrease the porosity of the device. Increasing band width can also diminish graft member wrinkling between coupling member turns. A number of tape members having different widths can be applied to a stent member, e.g., a first tape member having a first width and a second tape member having a second width different from the first width can be utilized.

The tape member (or separate pieces thereof) also may surround the terminal end portions of the stent-graft to secure the terminal portions of the graft member to the stent member.

Figure 6A:
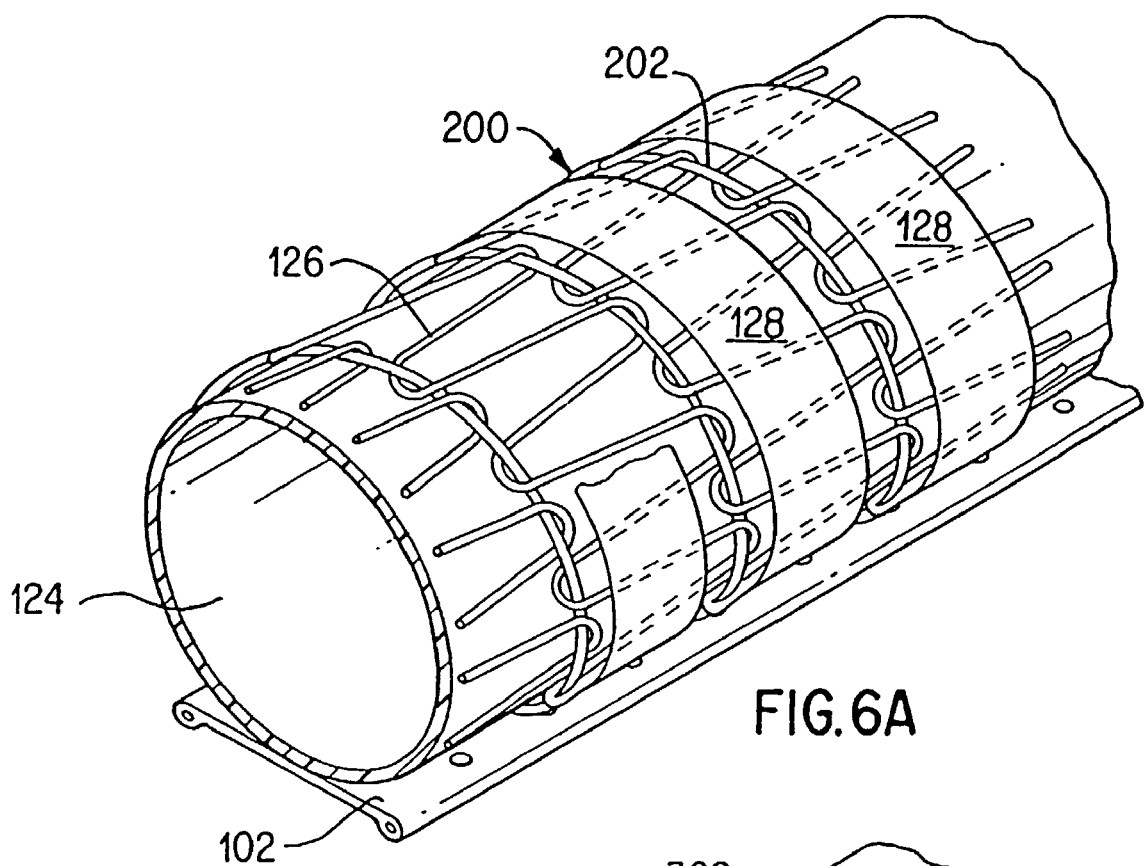
FIG. 6A is a perspective view of another embodiment of the implant in conjunction with the restraining member of FIG. 1.
Figure 6B:
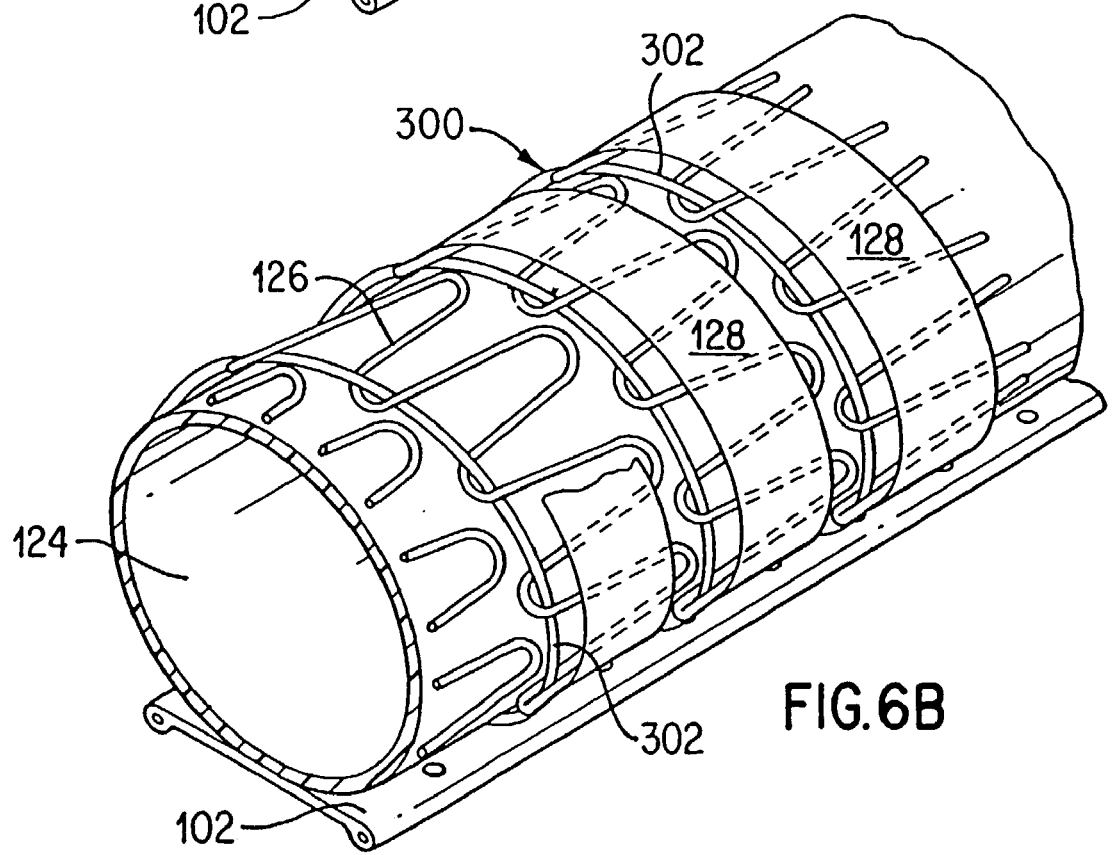
FIG. 6B is a perspective view of a further embodiment of the implant in conjunction with the restraining member of FIG. 1.

FIGS. 6A and 6B illustrate further stent-graft constructions that may be used with the delivery systems described herein. Referring to FIG. 6A, stent-graft (200) is the same as stent-graft (106) with the exception that stent-graft (200) includes a filament that couples stent undulations in adjacent turns. Filament (202) is laced or interwoven between undulations of the stent member and acquires a helical configuration (i.e., it forms a secondary helix) in being laced as such. Such a configuration is disclosed in PCT publication No. WO 95/26695 (International Application No. PCT/US95/04000) the entirety of which is hereby incorporated herein by reference. The stent-graft (300) shown in FIG. 6B is the same as that shown in FIG. 6A with the exception that the filament (302) is interwoven between undulations in the same helical turn of the stent member.

The filaments (202, 302) are of the same construction and may be of any appropriate filamentary material which is blood compatible or biocompatible and sufficiently flexible to allow the stent to flex and not deform the stent upon folding. Although the linkage may be a single or multiple strand wire (platinum, platinum/tungsten, gold, palladium, tantalum, stainless steel, etc.), much preferred is the use of polymeric biocompatible filaments. The flexible link may be tied-off at either end of the stent-graft (200), for example, by wrapping its end portion around the stent and tying it off at the point at the beginning of the last turn as would be apparent to one of ordinary skill.

A percutaneously delivered stent-graft must expand from a reduced diameter, necessary for delivery, to a larger deployed diameter. The diameters of stent-grafts obviously vary with the size of the body lumen into which they are placed. For instance, the stents typically may range in size from 2.0 mm in diameter (for neurological applications) to 40 mm in diameter (for placement in the aorta). A range of about 2.0 mm to 6.5 mm (perhaps to 10.0 mm) is believed to be desirable. Typically, expansion ratios of 2:1 or more are required. These stents are capable of expansion ratios of up to 5:1 for larger diameter stents. Typical expansion ratios, for instance, typically are in the range of about 2:1 to about 4:1. The thickness of the stent materials obviously varies with the size (or diameter) of the stent and the ultimate required yield strength of the folded stent. These values are further dependent upon the selected materials of construction. Wire used in these variations are typically of stronger alloys, e.g., nitinol and stronger spring stainless steels, and have diameters of about 0.002 inches to 0.005 inches. For the larger stents, the appropriate diameter for the stent wire may be somewhat larger, e.g., 0.005 to 0.020 inches. For flat stock metallic stents, thicknesses of about 0.002 inches to 0.005 inches is usually sufficient. For the larger stents, the appropriate thickness for the stent flat stock may be somewhat thicker, e.g., 0.005 to 0.020 inches.

The following example is provided for purposes of illustrating a preferred method of manufacturing a stent-graft as shown in FIG. 3. It should be noted, however, that this example is not intended to be limiting. The stent member wire is helically wound around a mandrel having pins positioned thereon so that the helical structure and undulations can be formed simultaneously. While still on the mandrel, the stent member is heated to about 460° F. for about 20 minutes so that it retains its shape. Wire sizes and materials may vary widely depending on the application. The following is an example construction for a stent-graft designed to accommodate a 6mm diameter vessel lumen. The stent member comprises a nitinol wire (50.8 atomic % Ni) having a diameter of about 0.007 inch. In this example case, the wire is formed to have sinusoidal undulations, each having an amplitude measured peak-to-peak of about 0.100 inch and the helix is formed with a pitch of about 10 windings per inch. The inner diameter of the helix (when unconstrained) is about 6.8 mm. (The filament when used as shown in FIGS. 6A and 6B may have a diameter of about 0.006 inch.)

In this example, the graft member is porous expanded polytetrafluorethylene (PTFE), while the tape member is expanded PTFE coated with FEP. The tape member is in the form of a flat ribbon (as shown in the illustrative embodiments) that is positioned around the stent and graft member as shown in FIG. 3. The side of the tape member or ribbon that is FEP coated faces the graft member to secure it to the graft member. The intermediate stent-graft construction is heated to allow the materials of the tape and graft member to merge and self-bind as will be described in more detail below.

The FEP-coated porous expanded PTFE film used to form the tape member preferably is made by a process which comprises the steps of:

(a) contacting a porous PTFE film with another layer which is preferably a film of FEP or alternatively of another thermoplastic polymer;

(b) heating the composition obtained in step (a) to a temperature above the melting point of the thermoplastic polymer;

(c) stretching the heated composition of step (b) while maintaining the temperature above the melting point of the thermoplastic polymer; and (d) cooling the product of step (c).

In addition to FEP, other thermoplastic polymers including thermoplastic fluoropolymers may also be used to make this coated film. The adhesive coating on the porous expanded PTFE film may be either continuous (non-porous) or discontinuous (porous) depending primarily on the amount and rate of stretching, the temperature during stretching, and the thickness of the adhesive prior to stretching.

In constructing this example, the thin wall expanded PTFE graft was of about 0.1 mm (0.004 in) thickness and had a density of about 0.5 g/cc. The microstructure of the porous expanded PTFE contained fibrils of about 25 micron length. A 3 cm length of this graft material was placed on a mandrel the same diameter as the inner diameter of the graft. The nitinol stent member having about a 3 cm length was then carefully fitted over the center of the thin wall graft.

The stent-member was then provided with a tape coupling member comprised of the FEP coated film as described above. The tape member was helically wrapped around the exterior surface of the stent-member as shown in FIG. 3. The tape member was oriented so that its FEP-coated side faced inward and contacted the exterior surface of the stent-member. This tape surface was exposed to the outward facing surface of the thin wall graft member exposed through the openings in the stent member. The uniaxially-oriented fibrils of the microstructure of the helically-wrapped ribbon were helically-oriented about the exterior stent surface.

The mandrel assembly was placed into an oven set at 315° C. for a period of 15 minutes after which the film-wrapped mandrel was removed from the oven and allowed to cool. Following cooling to approximately ambient temperature, the mandrel was removed from the resultant stent-graft. The amount of heat applied was adequate to melt the FEP-coating on the porous expanded PTFE film and thereby cause the graft and coupling members to adhere to each other. Thus, the graft member was adhesively bonded to the inner surface of the helically-wrapped tape member through the openings between the adjacent wires of the stent member. The combined thickness of the luminal and exterior coverings (graft and tape members) and the stent member was about 0.4 mm.

Although the delivery systems have been described with reference to the stent-graft examples illustrated in the drawings, it should be understood that it can be used in conjunction with other devices, stents or stent-grafts having constructions different than those shown. For example, delivery systems described herein may be used in conjunction with bifurcated stents or stent-grafts as will be described in detail below. In addition, although a self-expanding stent-graft has been described, balloon expanding stent-grafts also may be used in conjunction with the delivery systems described herein. These stent-grafts require a balloon to expand them into their expanded state as opposed to the spring energy stored in a collapsed self-expanding stent.

Figure 7A:
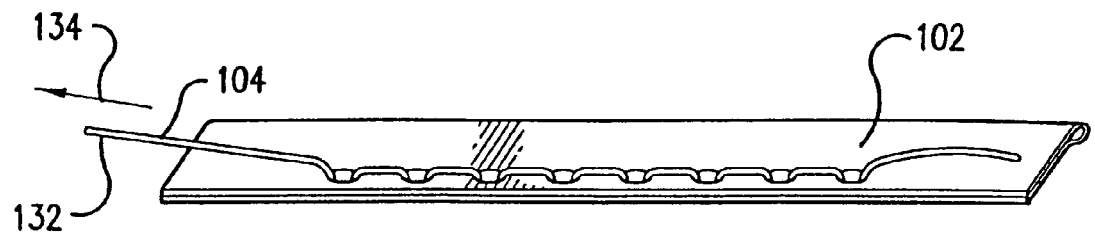
FIG. 7A illustrates the restraining and coupling member of FIG. 1 and the pull direction for removing the coupling member from the restraining member.
Figure 7B:
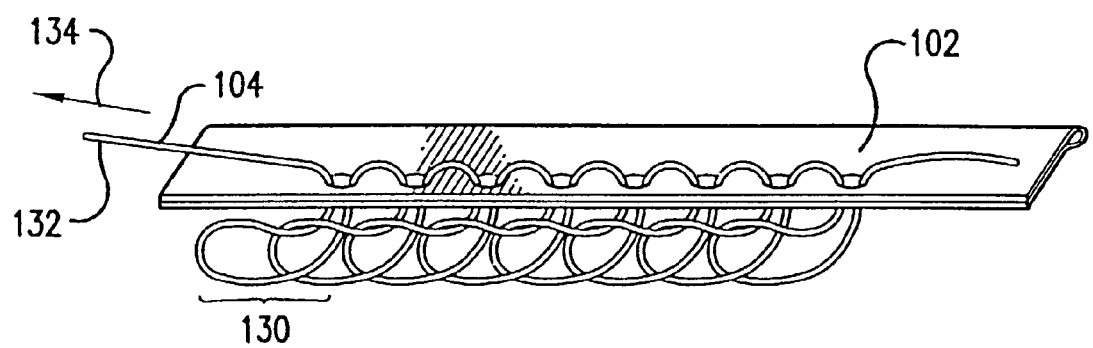
FIG. 7B shows the assembly of FIG. 7A with the coupling member loosened to illustrate the chain knots.
Figure 7C:
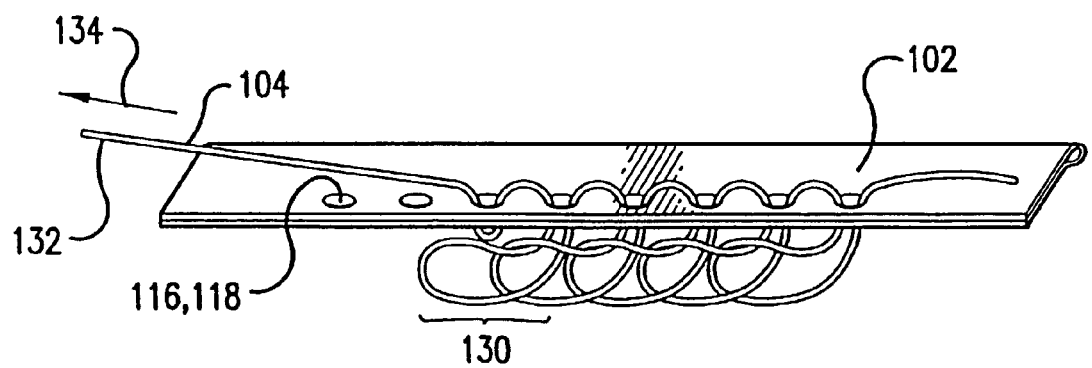
FIG. 7C diagrammatically represents release of the assembly of FIG. 7A or 7B as the coupling member is pulled in the direction shown.

Referring to FIGS. 7A-C, one slip knot configuration that may be used in conjunction with the thread-like coupling member (104) will be described. The restraining member (102) is shown without an implant positioned therein for purposes of simplification. FIG. 7A illustrates the slip knot in a prerelease or predeployment state. The series of knots are generally flush with the restraining member (102) surface and add very little profile to the construct which is preferred during implant delivery. FIG. 7B shows the assembly of FIG. 7A with the thread-like coupling member (104) loosened to illustrate how the chain knots (130) may be formed. FIG. 7C diagrammatically represents release of the assembly of FIG. 7A or 7B. The illustrated stitch is releasable by pulling one end of the line that results in releasing of the cylindrical or tubular restraining member and then deployment of the device. This particular stitch is called a chain stitch and may be created with a single needle and a single line. A chain stitch is a series of loops or slip knots that are looped through one another such that one slip knot prevents the next slip knot from releasing. When the line is pulled to release a slip knot, the following slip knot is then released and that releases the next slip knot. This process continues during pulling of the line until the entire line is pulled out of the restraining member.

Referring to FIGS. 7A-C, as the unknotted portion or the lead (132) of the thread-like coupling member (104) is pulled, such as in the direction shown by reference arrow (134), each consecutive chain knot (132) releases the next adjacent one. In the preferred embodiment, the chain knots (130) of the coupling member (104) are arranged to progressively release the collapsed implant in a direction away from the distal portion of the delivery catheter as shown in FIG. 10A and as will be discussed in detail below.

Figure 8A:
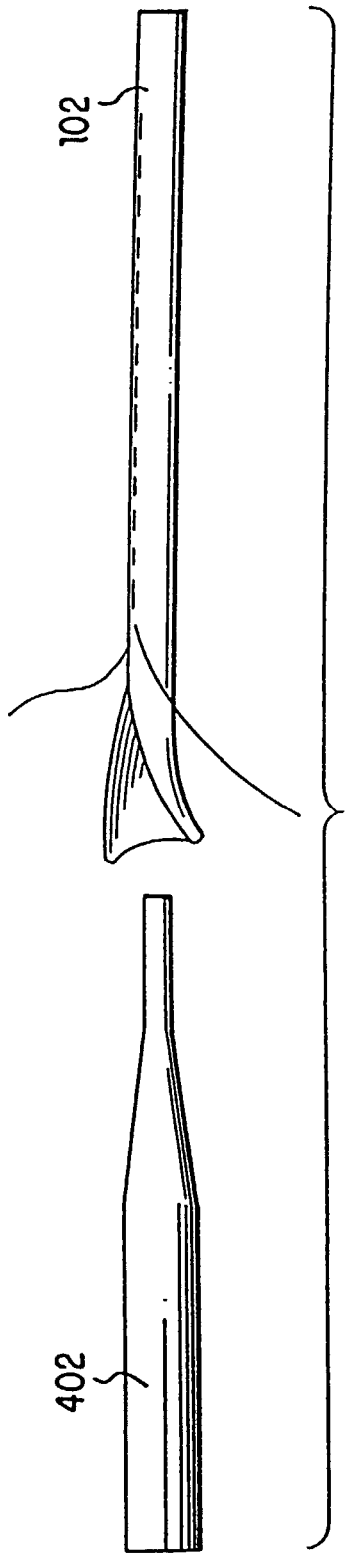
Figure 8B:
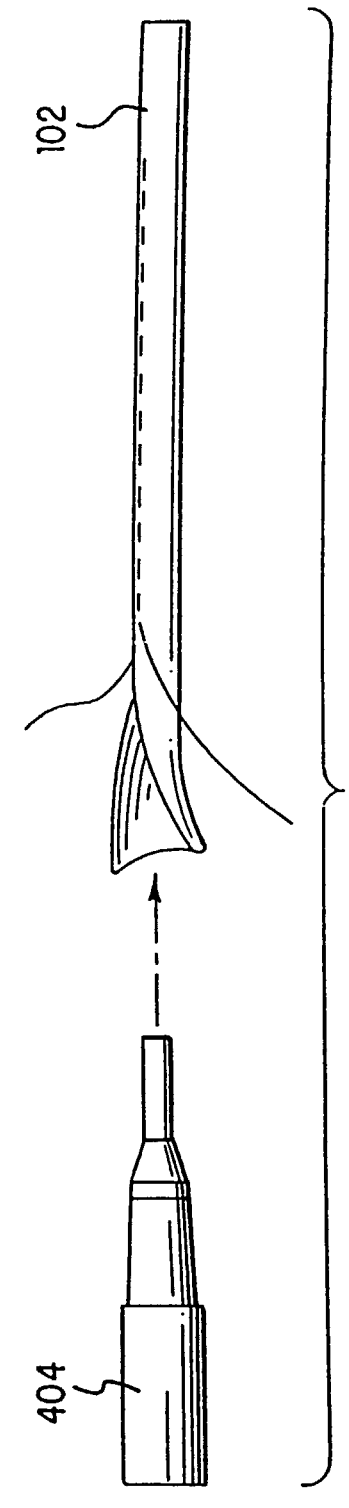
Figure 8C:
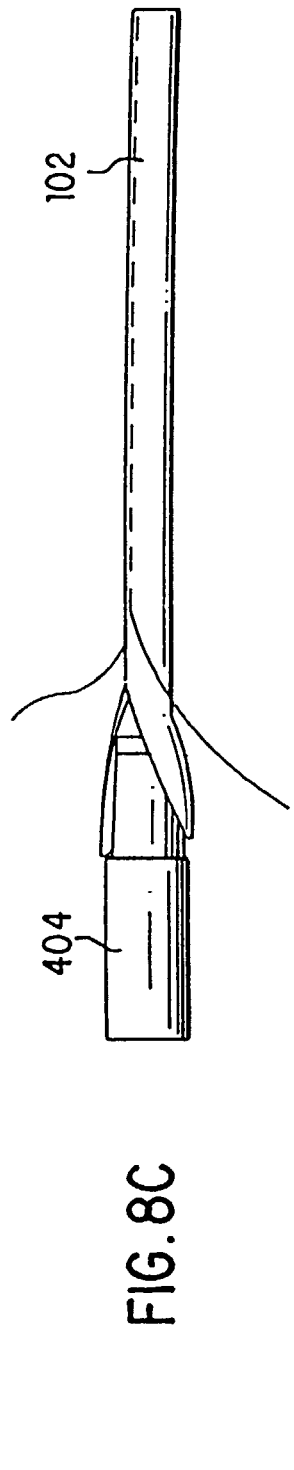

Referring to FIGS. 8A through 8F, a method for making an assembly comprising a restraining member with a collapsed or compressed implant therein is shown for purposes of example. FIG. 8A shows the restraining member (102) with its side margins releasably coupled to one another and its left end dilated by a tapered mechanical dilator (402). A small funnel (404) is then inserted into the restraining member (102) as shown in FIGS. 8B and 8C. The small funnel (404) and restraining member (102) are then mounted onto a pulling frame (410), and a large funnel (406) is fitted into the small funnel (404) as shown in FIG. 8D. Traction or pull lines (408), which have been sutured to one end of the stent-graft, (106) are pulled through the large funnel (406), small funnel (404), and restraining member (102) with a tapered mandrel (416). As shown in FIG. 8F, the pull lines (408) are fastened to a tie down post (412) located on a tension screw (414) and then are pulled by the tension screw (414). The stent-graft (106) is then pulled and collapsed sequentially through the large (406) and small (404) funnels, and then into the restraining member (102). Once the stent-graft (106) has been radially collapsed into the restraining member (102), which has its side margins coupled together, the pull lines (408) can be removed. The mandrel (416) may be inserted into the restrained implant to facilitate introduction of another component. In the preferred embodiment, a multilumen catheter (136) (FIGS. 9-11) is introduced through the center of the compressed stent-graft (106) and is used to deliver the radially restrained stent-graft to the desired endolumenal site.

It also is noted that the funnels may be chilled to facilitate compression of the stent when the stent is made of nitinol. That is, when the stent is made of nitinol, the funnels may be chilled below 0° C. or below the transition temperature (Mf) where nitinol is in its martensitic state. In addition, the stent-graft could be folded first and then reduced in profile by pulling through the funnel and into the restraining member. Cooling may be accomplished by spray soaking the stent-graft with chilled gas such as tetrafluroethane. Micro-Dust™ dry circuit duster manufactured by MicroCare Corporation (Conn) provides suitable results. The spray canister preferably is held upside down to discharge the fluid as a liquid onto the stent-graft.

A method of deploying an implant will be described with reference to FIGS. 9-11. In general, an implant may be delivered percutaneously with the delivery systems described herein, typically through the vasculature, after having been assembled in the reduced diameter form (see e.g. FIG. 1). At the desired delivery site, the implant may be released from the restraining member, thus allowing the implant to expand or be expanded against the lumen wall at the delivery site. Although other devices including stents or stent-grafts may be used, such as balloon expandable stents, the following example will be made with reference to a selfexpanding stent-graft, which has the ability to fully expand itself into its final predetermined geometry when unconstrained. More particularly, the following example will be made using a delivery system as shown in FIGS. 1 and 7A-C and a stent-graft construction as shown in FIG. 3.

Referring to FIGS. 9A and 9B, an implant delivery assembly including a collapsed stent-graft (106) that is confined within a restraining member (102) and, which surrounds a distal portion of the delivery catheter (136), is shown. The attending physician will select a device having an appropriate size. Typically, the stent-graft will be selected to have an expanded diameter of up to about 20% greater than the diameter of the lumen at the desired deployment site.

The delivery catheter preferably is a multilumen catheter. The proximal portion of the catheter (136) is coupled to a hub (140), which includes a guidewire port (142) for a guidewire (142), and a deployment knob (144), which is coupled to the lead (132) of the thread-like coupling member (104). Accordingly, when the knob (144) is retracted, the restraining member (102) is released so that the stent-graft may expand. The hub (140) also may include a flushing port (146) as is conventional in the art. The stent-graft (106) is held axially in place prior to deployment by a proximal barrier (148) and distal barrier (150) which are positioned around delivery catheter (136) adjacent to the proximal and distal portions, respectively, of the restrained stent-graft. The proximal and distal barriers (148, 150) may be fixedly secured to the multilumen catheter (136) to restrict any axial movement of the restrained stent-graft. The barriers preferably are positioned to abut against the stent-graft or restraining member. The lead (132) of the coupling member (104) is passed through an aperture (152) in the proximal barrier (148) which is fluidly coupled to a lumen in the delivery catheter (136) so that the coupling member lead (132) can be coupled to the deployment knob (144). FIGS. 9A and 9B show advancement of the catheter (136) and the restrained implant through a vessel (154) toward a desired site. Referring to FIGS. 10A and 10B, once the restrained stent-graft reaches the desired site (156), the deployment knob (144) is retracted so that the stent-graft progressively expands as shown in the drawings as the coupling member (104) is removed from the restraining member. The coupling member preferably is arranged to facilitate stent-graft expansion in a direction from the distal to proximal ends of the stent-graft (i.e., in a direction from the catheter tip to the catheter hub). FIGS. 11A and 11B show the stent-graft (106) and restraining member (102) in their final implantation position after the coupling member and catheter have been removed therefrom. In another embodiment, multiple restraining members may be used as shown in FIG. 9C. When the multiple coupling members (104) are released simultaneously implant deployment time may be reduced.

A method for deploying a balloon expandable stent-graft may be the same as that described above, with the exception that after the coupling member (104) has been retracted from the eyelets (116), the balloon, which may be positioned inside the stent-graft prior to delivery, is inflated to expand the stent-graft (106) and then deflated for removal through the catheter (136).

According to further embodiments, multidirectional coupling member release or multiple coupling members may be used. These configurations may facilitate more rapid deployment of the implant than when a single unidirectional coupling member is used. FIGS. 12A-12D diagrammatically show multidirectional deployment of a restrained implant where a coupling member arrangement is provided to release the implant from its middle portion, preferably its axial center, outward toward the implant ends. Although a particular coupling member configuration is not shown in these diagrammatic representations, one suitable coupling configuration is shown in FIG. 13 where the leads (132) may be passed through the aperture (152) and coupled to the deployment knob (144) as shown in FIG. 9A and described above.

Figure 12A:
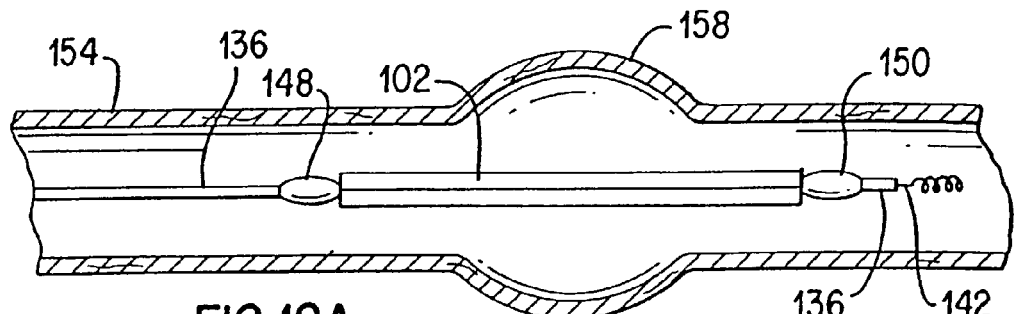
FIGS. 12A, 12B, 12C and 12D diagrammatically show deployment of a restrained implant where the coupling member configuration provides release from the middle portion of the implant outward toward the implant ends.
Figure 12B:
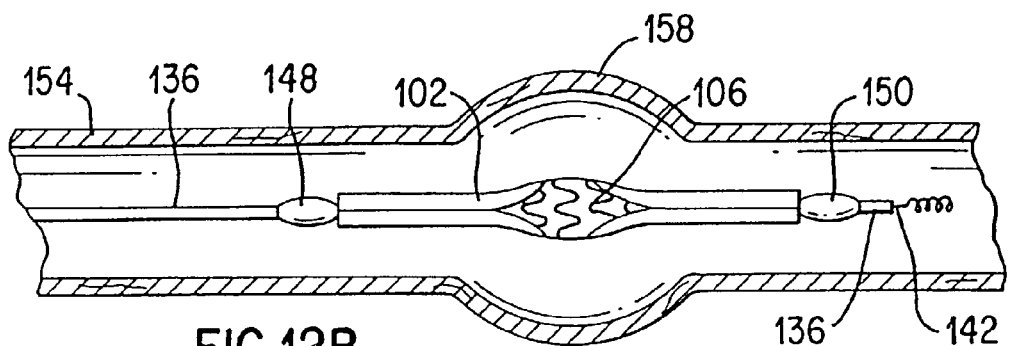
Figure 12C:
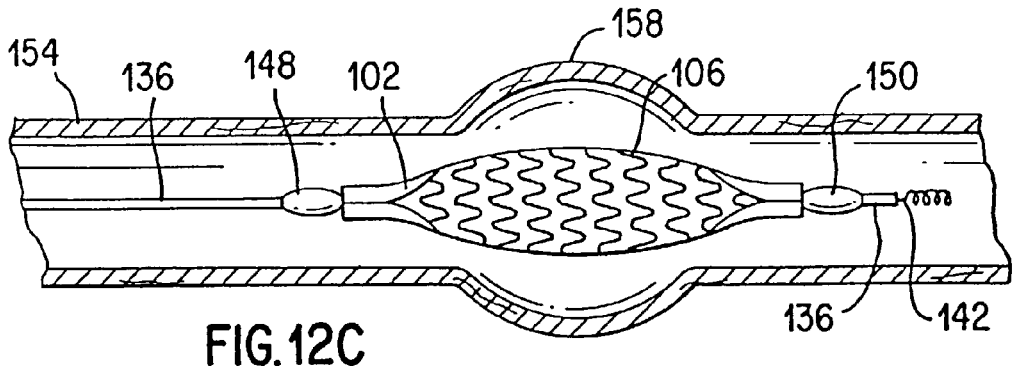
Figure 12D:
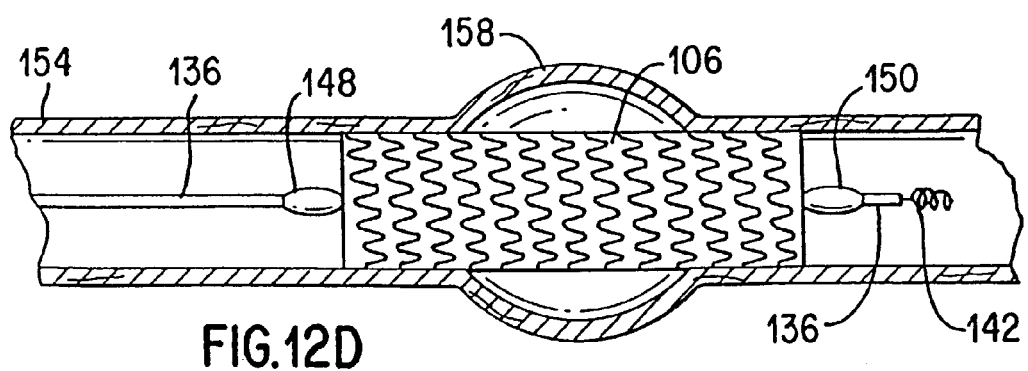

Referring to FIG. 12A, the restrained stent-graft, which is positioned on the distal end portion of delivery catheter (136), is advanced through a vessel (154) for deployment in an aneurysm (158). The axial midpoint of the restraining member (102) preferably is positioned at the center of the aneurysmal sac. As the coupling member arrangement unlacing propagates from middle of the construct toward the proximal and distal ends of the restraining member (102) and the stent-graft (106), the stent-graft (106) progressively expands from its axial midportion toward its ends as shown in FIGS. 12B and 12C. This may be accomplished by pulling the leads (132) shown in FIG. 13 simultaneously when the arrangement in that figure is used. The stent-graft size is selected so that when the restraining member is fully released and the stent-graft fully deployed as shown in FIG. 12D, the proximal and distal portions of the stent-graft are positioned against the proximal and distal necks of the aneurysm. The delivery catheter may then be retracted.

As is apparent from the drawings, this embodiment advantageously allows fluid flow through the aneurysmal sac to remain substantially unobstructed during the release of the restraining member. For example, the stent-graft ends are still constrained at the deployment time shown in FIG. 12C where the aneurysm neck regions are shown minimally obstructed. In addition, this simultaneous, multidirectional release of the restraining member advantageously reduces the time in which fluid flow in the vessel may disturb the implant position as it is deployed as compared to a single directional release mechanism such as that shown in FIGS. 9-11.

Referring to FIG. 13, a multiple coupling member configuration is shown. The illustrated arrangement includes two lacing configuration (151) and (153). Except for the placement of the lead (132) of thread-like coupling member (104), configuration (153) is the mirror image of configuration (151). Each of the lacing configurations (151 & 153) is the same as that shown in FIGS. 7A-C with the exception that each configuration (151 & 153) further includes two additional slip knots, generally designated with reference numeral (504), and tuck or loop arrangement (506). The additional slip knots are not interwoven in the restraining member and provide a delay mechanism for release of the coupling member, as is apparent from the drawings, when the lead (132) is pulled in the direction of the arrow (134). Thus, inadvertent pulling of the lend (132) will not immediately begin to release the coupling member from the restraining member. The tuck arrangement simply involves tucking the slack from lead (132) under stitches at various intervals as shown so that the additional slip knots (504) may be pulled out of the way for delivery. In addition, the tuck or loop arrangement (506) provides an additional delay mechanism for release of the slip knots.

Bifurcated Stent or Stent-Graft

The following describes a modular bifurcated stent-graft constructed for treating a bifurcation site within a mammalian body. The stent-graft components generally comprise a flexible graft member attached to a wire stent member using a tape member according to the principles discussed at length above. Preferably the stent-graft components are designed for compressed delivery and are self-expanding, in the manner described above.

The modular stent-graft of FIGS. 14A through 14D generally has two principal components; a main body (700) and a contralateral leg (730) each generally having a graft member attached to a stent member according to the description above. The main body (700) generally has a number of sections which have distinct overall constructions. A distal trunk section (708) has a single lumen structure beginning at a distal end (702) of the main body (700) and continuing until a bifurcation point (728). The bifurcation point (728) is the location within the prosthesis where the single lumen of the distal trunk section (708) bifurcates into internal two flow lumen.

An intermediate section (710) begins at the bifurcation point (728) and continues to the receiving hole (704). In the intermediate section (710), the stent-graft has an internal graft structure which is bifurcated into two lumen surrounded by a generally tubular, single-lumen stent structure. Finally, a proximal section (712) is a single lumen structure for both the stent member and the graft member and includes an ipsilateral leg (726) which terminates at an ipsilateral leg hole (706).

The graft member of the intermediate section (710) bifurcates the single lumen distal trunk section (708) into the ipsalateral leg (726) and am internal female receiving lumen (703). The receiving lumen (703) terminates at a receiving hole (704). The receiving hole (704) and receiving lumen (703) accommodate delivery and attachment of the contralateral leg component (730). Preferably, the graft material at the distal end (734) of the contralateral leg component (730) is scalloped as shown more clearly in FIG. 23 discussed below.

The receiving hole (704) is supported by a wire structure around a substantial portion of its periphery so that the receiving hole (704) is held open after deployment. In a preferred embodiment the wire structure that supports the receiving hole (704) is an independent wire ring (714).

The independent wire ring (714) is located in the general area of the receiving hole (704) in the intermediate section (710). The independent wire ring (714) ensures that the graft material at the receiving hole (704) is supported in an open position to receive the distal end (734) of the contralateral leg (730). In absence of such support, the receiving hole (704) may not reliably open after delivery of the main body component (700) because within the intermediate section (710) the bifurcated graft member in the area of the receiving lumen (703) does not have full stent support on its interior periphery. This may be better seen in FIG. 18 which shows the absence of any internal stent support of the interior graft periphery (785) in the area of the receiving lumen (703).

The independent wire ring (714) may be comprised of the same materials as the other stent-graft sections discussed above and is preferrably self-expanding. In a preferred embodiment, the independent wire ring comprises a single turn of an undulating wire stent material surrounded by at least one layer of tape which is heat bonded to the receiving hole (704). Alternatively, the independent wire ring (714) could be formed as the last turn of the main body (700).

A radiopaque marker may be used to make the receiving hole (704) visible during implantation. Such a marker may include a radiopaque wire adjacent to the independent wire ring (714). Such markers make it easier to see the location of the receiving hole (704) after deployment of the main body (700) within the mammalian body.

Figure 14A:
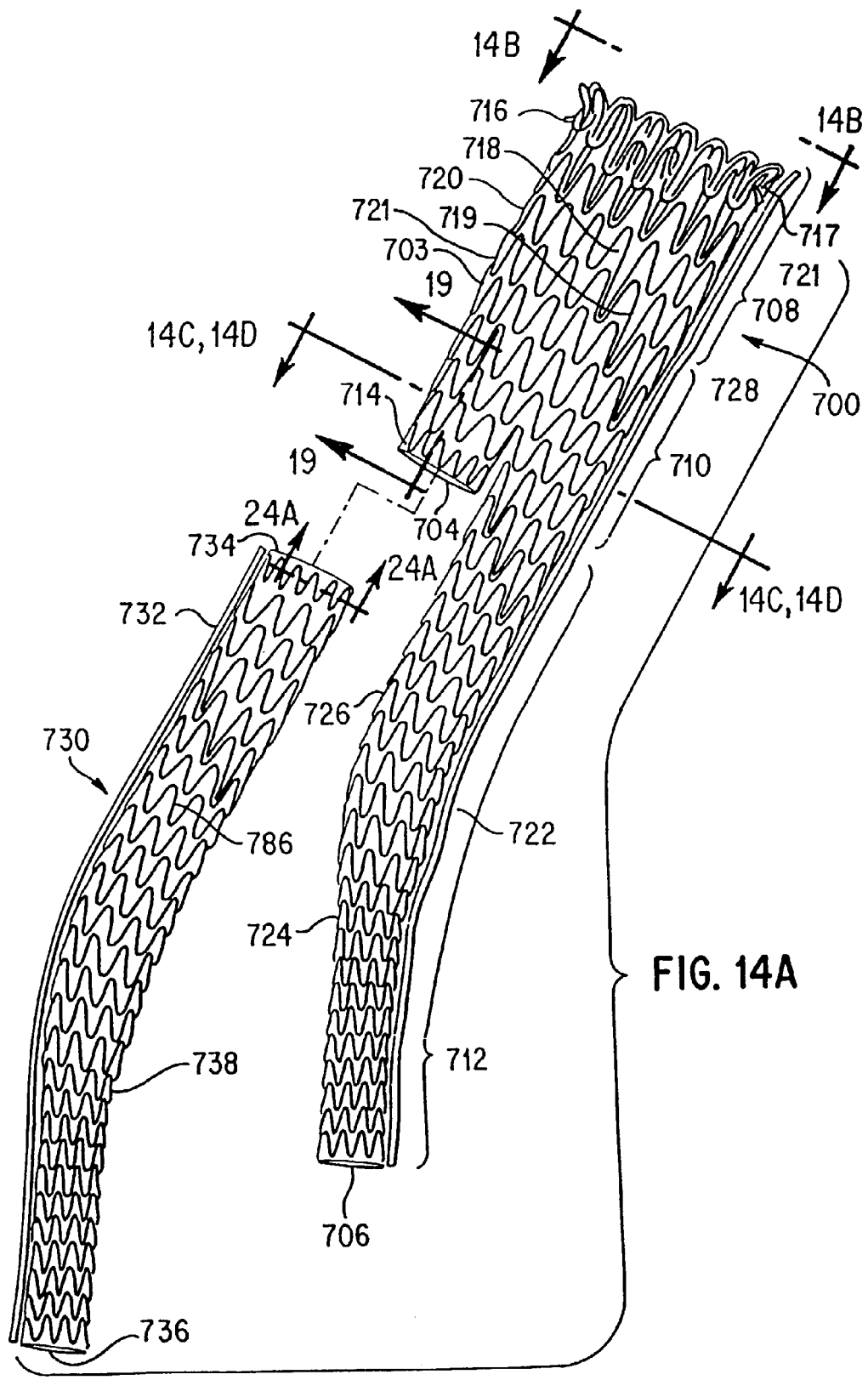
FIG. 14A is a perspective view of a bifurcated stent-graft in accordance with the principles of the present invention.
Figure 14B:
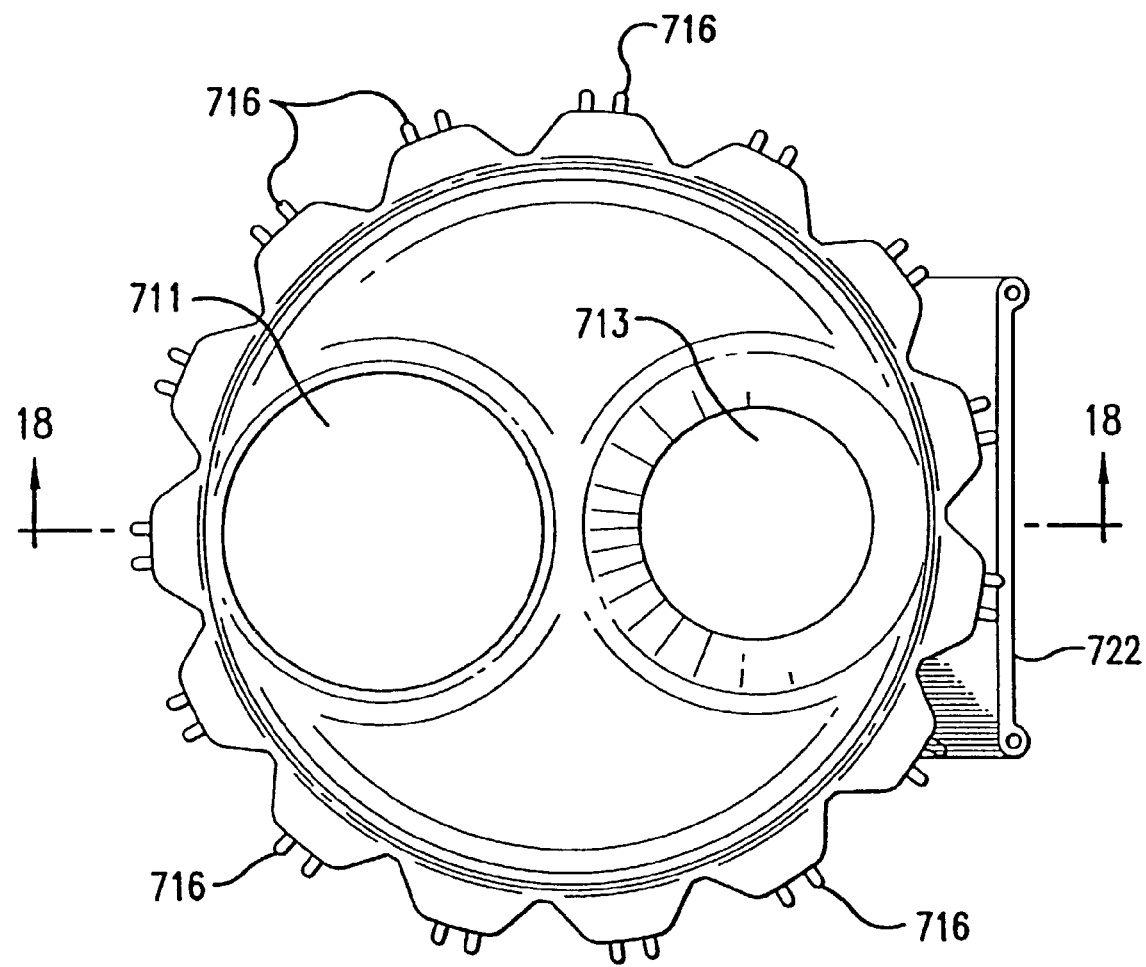
FIG. 14B is a top plan view of the bifurcated stent-graft of FIG. 14A.
Figure 14C:
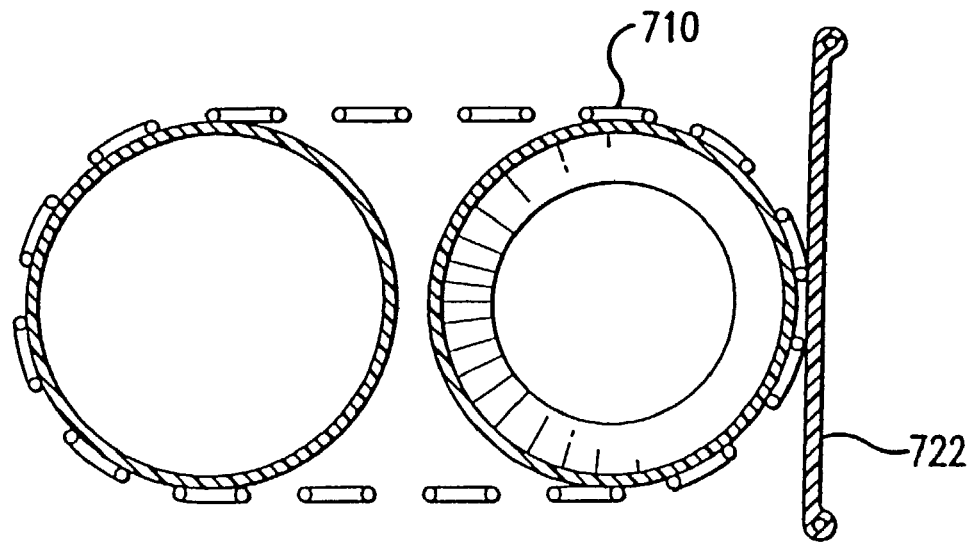
FIG. 14C is a cross-section view taken along section line 14C-14C depicted in FIG. 14A.

This construction of the intermediate stent section (710) as seen in cross-section in FIG. 14C is characterized by a single-lumen stent member and bifurcated graft member and offers both a smaller compressed profile as well as simplified manufacturing over constructions which have discreet stented leg features. The compressed profile is determined largely by the physical amount of stent and graft material present in a given section. This construction eliminates the stent material that would normally support the inside periphery of the bifurcated graft section resulting in less stent material to compress in that region. As the main body component (700) is compressed for delivery as discussed above, the compressed profile is significantly smaller than would be a structure that had a section of bifurcated stent over the section of bifurcated graft.

Even though bifurcated flow is supported, manufacturing is simplified because there is no bifurcated stent section. Winding a bifurcated stent section in one piece, for example, is a more complex process. Likewise, winding separate cylindrical stent structures and connecting them to form a bifurcated stent structure is complicated and ultimately may be less reliable. The intermediate section (710) allows the entire stent member that covers the main body component (700) to be made from a single undulating wire arranged in multiple helical turns. The result is a bifurcated stent-graft device which is simple to manufacture, easily compressible and which expands reliably upon deployment.

Figure 14D:
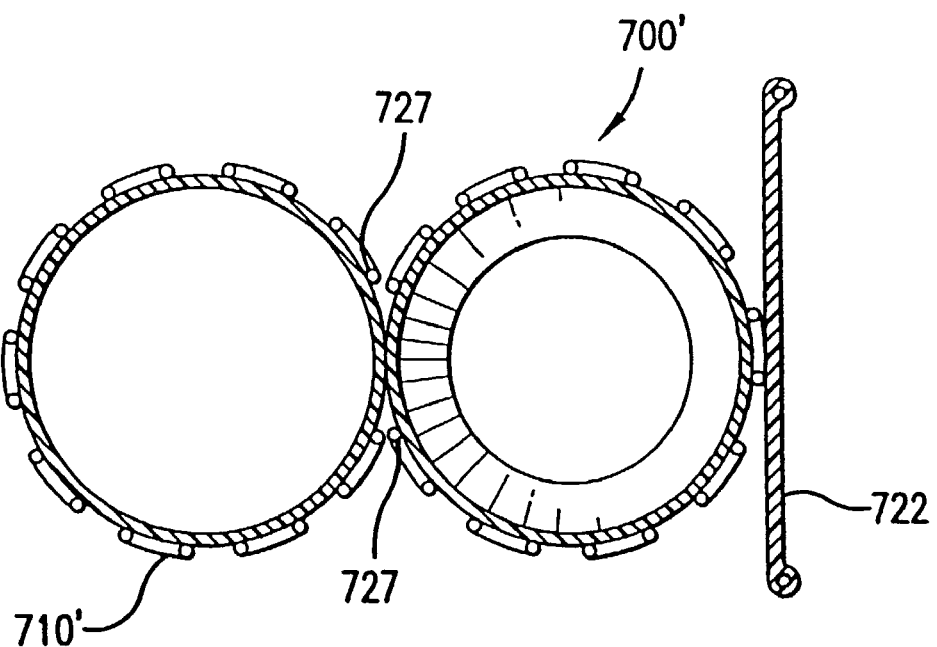
FIG. 14D is a cross-sectional view taken along section line 14D-14D depicted in FIG. 14A showing an alternate embodiment.

An alternate construction of the intermediate stent section (710), is shown in FIG. 14D. The intermediate stent section (710) has a shape characterized by the indented regions (727). The cross-sectional shape could generally be described as a 'figure-8', except that the area between the bifurcated graft member remains unsupported at its centermost region. This construction is still a single lumen stent construction and therefore maintains much of the benefits of reduced profile and simplified manufacturability while providing the bifurcated graft member with increased support around a greater portion of its perimeter. Further, indented portions (727) have less of a tendency to spring outward upon application of external forces.

As mentioned above, the main body component (700) and the contralateral leg component (730) are adapted for delivery in a compressed state to a bifurcation site within a body. For this purpose the main body component (700) is preferably equipped with a restraining member (722) constructed as described above. Likewise, the contralateral leg component (730) has an attached restraining member (732) These restraining members are typically sutured to the graft material at intervals down their length.

Figure 15:
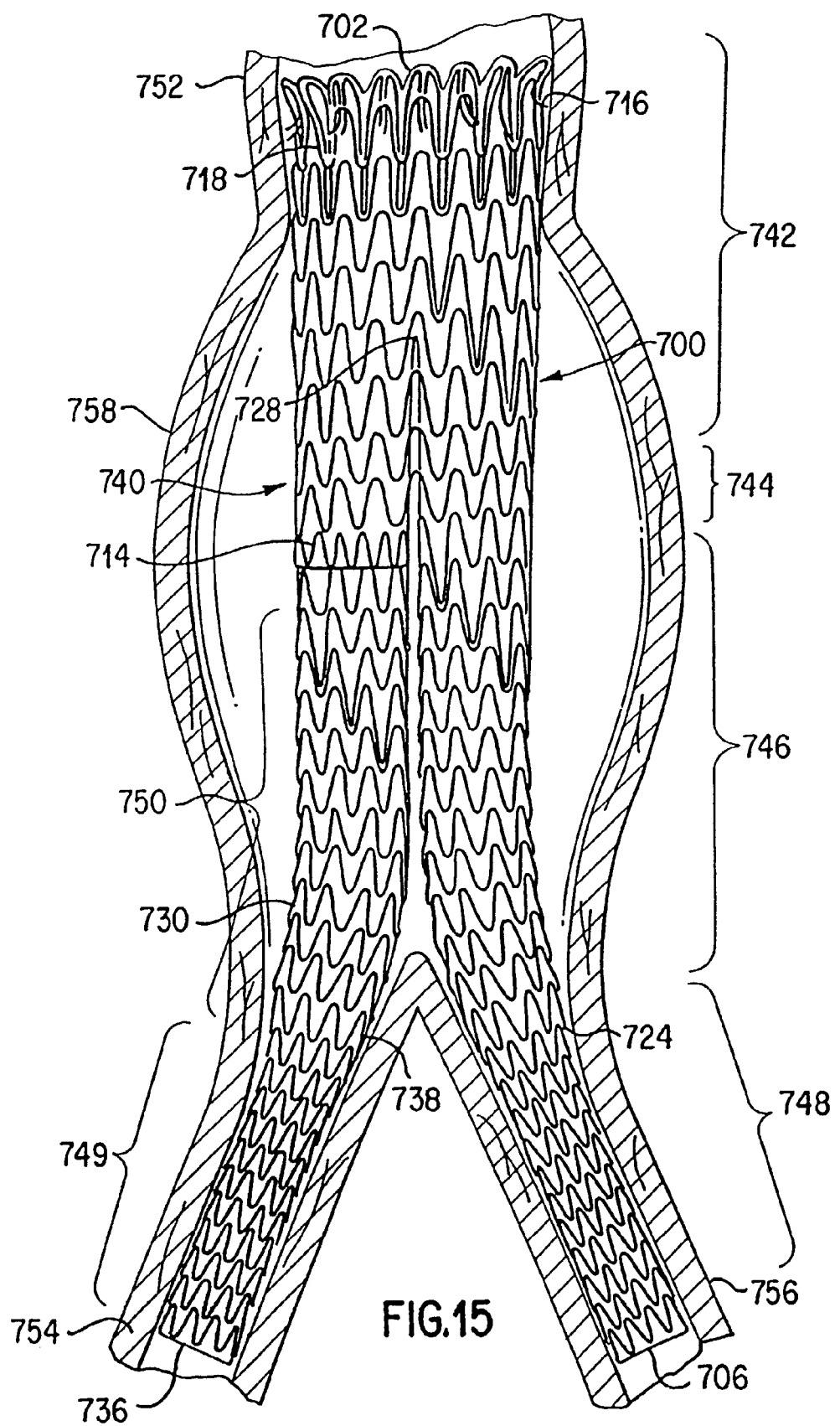
FIG. 15 is a front view of the assembled bifurcated stent-graft of FIG. 14A placed at a bifurcation site within the vasculature of a body.

FIG. 15 shows an assembled bifurcated stent-graft (740) after deployment at a bifurcation site within a bifurcated body vessel afflicted with an aneurysm (758). Although not intended to be so limited to any particular location, the inventive prosthesis is shown at the location where the abdominal aortic artery (752) bifurcates into the left iliac artery (756) and the right iliac artery (754). So that the various features of the inventive implant are more clearly shown, the restraining member is not shown in FIG. 15.

The assembled bifurcated stent-graft (740) is comprised of the main body component (700) and the contralateral leg component (730). The distal end (734) of the contralateral leg component (730) has been inserted into the receiving leg hole (704) and the female receiving lumen (703) of the main body component (700).

For best results in deploying any stent or stent-graft of these types it is essential that they have the appropriate structural properties such as axial stiffness, flexibility and kink-resistance. With complicated structures, such as those required for treating a bifurcated site, it is increasingly difficult to obtain the desired structural properties because optimizing one may negatively effect the other.

For instance, optimizing the global axial stiffness of a stent or stent-graft will necessarily make the device significantly less flexible and consequently impair its resistance to kinking and lessen its ability to conform to the natural bends of curves the body's vasculature. Conversely a device that has high flexibility with little axial stiffness is difficult to properly deploy and does not aid in anchoring the device in the desired location.

With these constraints in mind, it has been discovered that having a bifurcated stent-graft which has segments constructed with varying structural properties offers improved deployability, is less susceptible to kinking, and favorably tends to maintain its desired position after deployment while allowing sufficient flexibility to accommodate movement by the body. The exact structural properties desired may depend on the location where the prosthesis is to be deployed.

For these reasons, it is preferable that the bifurcated stent or stent-graft be constructed with at least two segments having structural properties different from one another. For example, in FIG. 14A, a length of the distal section (708) and the intermediate section (710) may be constructed with a higher axial stiffness for improved deployment and positional stability while the proximal section (712) may be constructed to have higher flexibility to accommodate the geometry of the iliac artery.

It may be further desirable to have a number of segments that have different structural properties. Accordingly, the main body component (700) and the contralateral leg component (730) of the assembled stent-graft (740) have segments constructed with structural properties different from adjacent segments. In one preferred embodiment shown in FIG. 15, the main body component (700) has four different segments constructed with different structural properties. The distal segment (742) is constructed to have higher axial stiffness than the more flexible proximally adjacent segment (744). The proximal section (748) is constructed to have a higher flexibility than that of its distally adjacent segment (746). Likewise the contralateral leg component (730) has an axially stiffer distal segment (750) and a more flexible proximal segment (749).

There are a number of ways to alter the structural properties of stent or stent-graft components. One way of selectively altering the structural properties of a stent-graft segment is to use a tape member for that segment that has different physical dimensions. Such a tape member is discussed above with reference to the tape member (128) of FIG. 3. For example the tape member width, thickness or spacing may be increased, from the preferred dimensions discussed above, in a segment where it is desirable to have increased or decreased stiffness. For example, the use of wider tape wound with closer spacing will increase the stiffness in that area.

Another way of selectively altering the structural properties of a stent or stent-graft segment is shown in FIGS. 14A and 15. Extended struts (718) and (719) may be used to increase the axial stiffness of a stent-graft segment. Extended struts are formed by extending an apex on one turn of the undulating wire until it contacts an apex on an adjacent turn. This contact between an extended strut and the apex of an adjacent stent turn provides an added amount of axial stiffness. In a preferred embodiment, a layer of tape (not shown) is applied around the device in a helical pattern that covers each of the apexes of the extended struts. This additional layer of taping keeps the strut pairs together.

Referring to FIG. 14A, a first helical stent turn (720) and a second helical stent turn (721) have a generally undulating shape having apexes. An extended strut (718) of the stent turn (720) is formed having its apex near or in contact with the apex of the stent turn (721) directly below. The extended strut (719) is similarly formed by extending an apex of the stent turn (721) directly down to contact the apex in the turn below. This pattern in continued, each time spacing the extended strut over one undulation. This results in a helical pattern of extended struts down the length of the device. Of course, the extended struts may be arranged in patterns other than the helical configuration described.

A number of these patterns may be employed in any one segment or the extended strut pattern may be used in other segments to increase axial stiffness. Preferably the distally adjacent segment (746) on the main body component (700) and the axially stiff distal segment (750) on the contralateral leg component are constructed with extended struts as shown in FIG. 15.

Another important aspect of the present invention is achieving a secure position against the walls of the vessel lumen so that the deployed position is maintained and so that there is no leakage of luminal flow. Referring now to FIG. 15, the distal end (702) is sized to properly fit the inside diameter of the target artery, in this case the abdominal aortic artery. Typically the prosthesis is designed to have an unconstrained diameter slightly larger than the inside of the target vessel.

The ipsilateral and contralateral legs of the assembled bifurcated stent-graft (740) are typically the same size at their distal ends (around 13 mm for example) regardless of the size of the distal end (702) and undergo tapered sections (724) and (738) that taper to a diameter which corresponds approximately to the internal diameter of the iliac arteries. These tapered sections (724) and (738) are preferable to abrupt changes in diameter as they tend to produce superior flow dynamics.

After deployment, the assembled bifurcated stent-graft (740) must establish sufficient contact with the healthy vessel lumen an each side of the aneurysm (758) so that the device does not migrate or dislodge when subjected to the relatively high fluid pressures and flow rates encountered in such a major artery, especially when the body again becomes mobile after recovery. Further, sufficient contact must be made so that there is no leakage at the distal end (702), the ipsilateral leg hole (706) or the proximal end (736) of the contralateral leg.

Anchoring or staying features that allow the stent or stent-graft exterior to anchor itself to the vessel lumen wall may be provided to help the device seal to the vessel wall and maintain its deployed position. For example, anchors (716) as seen in FIGS. 14A and 15 are provided on the main body component (700) and could also be provided on the contralateral leg component (730). Preferably the top stent portion (717) is directed angularly outward. This flared stent portion works to force the anchors (716) into the vessel wall as the top stent portion (717) expands under force into radial interference with the vessel wall upon deployment.

Figure 17:
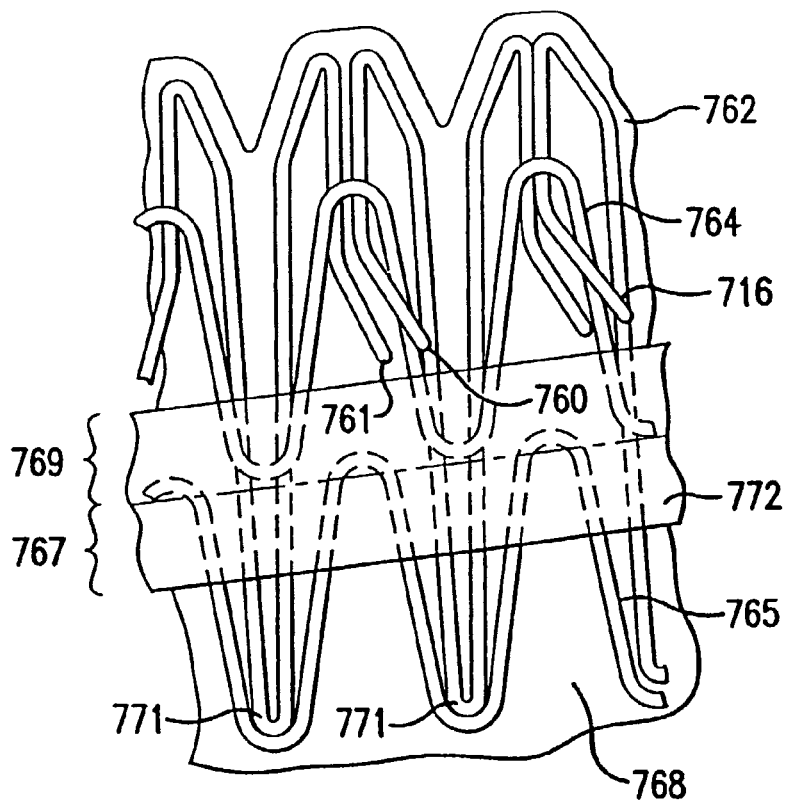
FIG. 17 is a perspective break-away view showing a close-up of a preferred construction of the stent anchors.

A preferred construction for an anchor (716) is shown in FIG. 17. This construction involves extending two wires from the upper stent turn (762) under an apex of an adjacent lower stent turn (764). The two ends of stent wires (760 and 761) are then bent out and away from the graft material (768). Extended struts (771) are formed adjacent to each anchor in the manner described above except the extended struts extend under the adjacent lower stent turn (764) down to a third stent turn (765). This extended strut arrangement provides support for the anchors (716) and provides for low stresses in the wires (760 and 761) under the application of bending forces encountered as the prosthesis expands into the vessel wall. The extended struts (771) minimize the localized deformation of the stent-graft structure in the area of the anchors by providing broader support.

Figure 16:
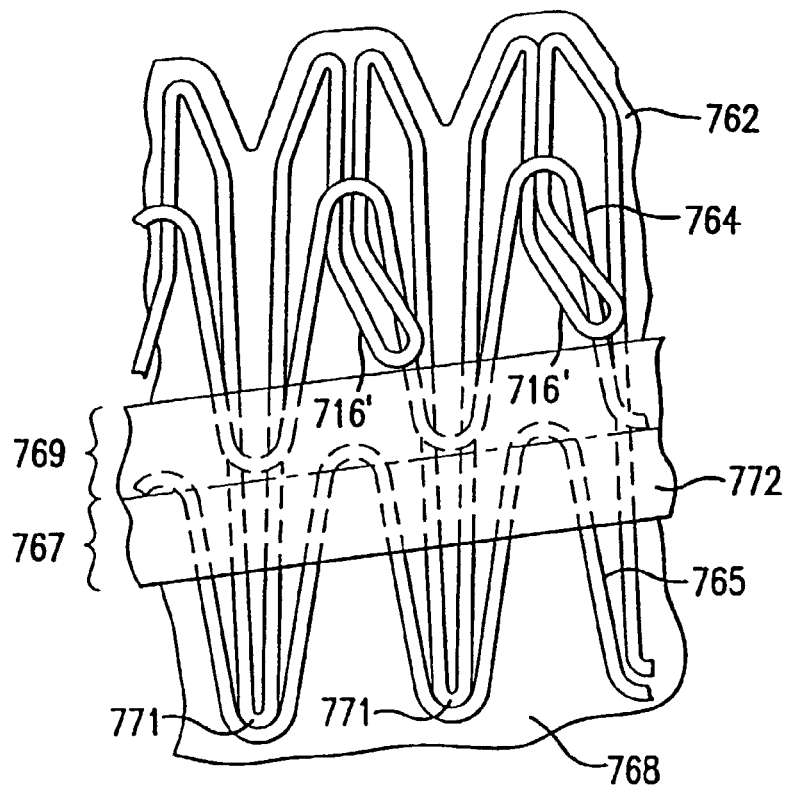
FIG. 16 is a perspective break-away view showing a close-up of one construction of stent anchors according to the present invention.

Another construction of the anchors (716') are shown in FIG. 16. An anchor (716') is formed in the same manner except the ends of the anchor remain connected in a 'U-shape' configuration as shown. An anchor (716') may be formed at any location on the stent-graft. Most preferably, the anchors are formed in an evenly spaced pattern around the top stent portion (717) (FIG. 14A).

It should be apparent that the anchors as described above are not limited in use to the stent-graft combination shown in the figures but indeed could be used in any non-bifurcated or stent only construction that require similar functionality.

Sealing at the vessel wall may also be enhanced by the alternate construction shown in FIG. 17 by way of a sealing mechanism. A sealing mechanism can be used with any type of implant, including any of the implants discussed above. For purposes of illustration, the sealing mechanism is shown with reference to the bifurcated implant of FIG. 14 and comprises seal member (772) as seen in detail in FIGS. 16 and 17. The sealing mechanism described below can be used with any of the implants discussed above.

One preferred construction for seal member (772) in the variations shown in FIGS. 16 and 17 may be similar to the preferred construction for the tape member used in constructing the stent-graft tubular member, as is provided in reference to FIG. 1 and FIG. 3 above.

In general, a thin walled ePTFE tape is used for seal member (772) similarly as that for tape member (128), shown variously in the previous figures. The tape used for seal member (772) is adhered to the outer surface of the stent-graft, including over tape member (128), described previously for bonding the stent and graft members. Seal member (772) has an inner surface constructed of a similar material for either the outer surface of the tape member (128) or the outer surface of the graft-member (124), depending upon which surface the seal member is desirably adhered.

First cuff end (767) is bonded to the stent-graft outer surface and second cuff end (769) is not, in order to form the unadhered flange to function as a one-way valve against peristent-graft flow. Seal member (772) may be selectively adhered along its length in this manner by providing a variable inner surface to the seal member such that, upon heating, only the surface in the region of first cuff end (767) bonds to the outer surface of the stent-graft. For example, the inner surface of seal member (772) may have an FEP liner in the region of first cuff end (767) but not in the region of second cuff end (769). In this case, upon contacting an outer surface of the stent-graft that has a uniform FEP outer surface, only first cuff end (767) may be heat secured thereon.

Alternatively, seal member (772) may have a uniform inner surface, such as constructed of FEP, and a variable outer surface, such as with a selective portion of FEP, may be provided either on the tape member (128) or on the graft member (124) in the region where the heat bonding of seal member (772) is desired. Still further, seal member (772) may have a uniform surface and may be positioned over tape member (128) and graft member (124) so that variability between the outer surfaces of tape member (128) and graft member (124) causes a selective bonding with the first cuff end (767) over one of those surfaces.

Further to the construction of seal member (772), the particular wall thickness of the tape which may be used for this component should desirably be as thin as possible to functionally provide the flange-one-way-valve function for that member. This is because, since seal member (772) is over the outer surface of the other stent and graft components of the stent-graft, seal member (772) is believed to be the profile-limiting feature of the overall assembly. Therefore, in a particular design, seal member (772) may desirably be a thinner wall than for the tape member used to construct the stent-graft described in reference to FIGS. 1 and 3.

Further referring to the particular constructions and related methods just described for adhering seal member (772) to the outer surface of the underlying stent-graft, it should be apparent to one of ordinary skill in the art that the desired construction and heat securing technique for seal member (772) is premised upon the theory that, where one polymer meets a like polymer (such as FEP meeting FEP), heating under proper conditions will allow for a selected heat bond. The present invention, however, should not be construed as limited to these particularly described conditions, but instead should be considered to more broadly encompass any suitable means for securing a seal member to the outer surface of a given tubular member, as would be apparent to one of ordinary skill, and as is provided previously with reference to FIGS. 16 and 17.

Further there is a plurality of circumferential strut spaces between the struts of the stent member. It is believed that these spaces may provide a path for leakage flow around the outer surface of the graft member and along the outside of the stent-graft. Second cuff end (769), however, captures such leakage flow beneath its flange, which can not propagate along the outer surface of the stent-graft because first cuff end (767) is secured to the outer surface of that stent-graft. In other words, flow over the stent-graft and into an aneurysm is occluded.

Furthermore, when apex strut (716) is anchored into the wall of abdominal aortic artery as shown in FIG. 15, it has been observed that the portion of main body component (700) at and adjacent to the apex strut (716) may be forced away from the artery wall. This action causes a separation between the outer surface of main body (700) and the artery wall, which separation is believed to create a leakage flow path. The flange of seal member (772) captures that flow and occludes it from propagating into the aneurysm (758).

In addition to maintaining a good contact with the vessel lumen walls, the components of the stent-graft must make sufficient contact with each other such that the separate modules stay attached and do not leak at their engagement interface. The inventive stent-graft shown in FIG. 18 illustrates several important features designed to effectuate a leak-free and positionally stable seal at the interface between the receiving lumen (703) of the main body component (700) and contralateral leg component (730).

FIG. 18 shows a partial cross-section of the assembled stent-graft. The contralateral leg component (730) has been inserted into the receiving lumen (703) of the main body component (700). This cross-sectional view shows clearly that the main body component (700) includes a main body graft member (780) and a main body stent member (782). The contralateral leg component (730) includes a contralateral graft member (784) and a contralateral stent member (786).

At the interface between the contralateral leg component (730) and the receiving lumen (703), the assembly provides for an extending sealing region (790). Preferably the extended sealing region (790) consists of a generally cylindrical interfering friction fit between the outside diameter of the contralateral leg component (730) and the inside diameter of the receiving lumen (703). That is, the natural or resting outside diameter of the self expanding contralateral leg component (730) would be larger than the natural inside diameter of the receiving lumen (703). Thus the forces created by the interference act to seal the two components and also serve to resist movement of the two components.

The type of generally cylindrical extended sealing region just described has many advantages. First, it allows for the stent and graft structures in the extended sealing region (790) to be constructed of relatively simple generally cylindrical elements that are easily manufactured. Because the extended sealing region (790) extends over a large length it necessarily has a large surface area to effectuate sealing between the components. This larger sealing area typically provides that multiple turns of the stent structures will be engaged in an interfering and thus sealing relationship.

In one preferred embodiment, the extended sealing region has a length in excess of one-half of the diameter of the receiving lumen (703), more preferably the length is greater that the diameter of the receiving lumen (703), and most preferably the length is more than 2 times the diameter of the receiving lumen (703).

Because the manufacturing tolerances of the simplified shapes are easily controlled and because the engagement of the extended sealing region (790) is quite large, a highly reliable joint is formed between the modular components. Even so it may be desirable to create one or more localized zones of increased interference to increase the sealing capability and positional stability.

Localized zones of interference may be created in a number of ways. In a preferred embodiment, an annular ring of decreased diameter is formed within the receiving lumen. Such a localized decreased diameter causes a greater interference with the outside diameter of the contralateral leg component in a localized area while the remainder of the engagement with the receiving lumen is subject to the general interference friction fit described above.

One way of creating a localized decreased diameter is illustrated in FIG. 20 which shows a partial cross-section of the extended sealing region (790). A zone of reduced diameter (799) is created by placing an anchoring ring (798) between the graft member (780) and the stent member (782) of the receiving lumen (703). The anchoring ring may be made from any polymeric or wire material, preferably a material that will not inhibit the receiving lumen from self-expanding to an open position. Most preferably the material is a suture material, typically ePTFE.

Figure 21:
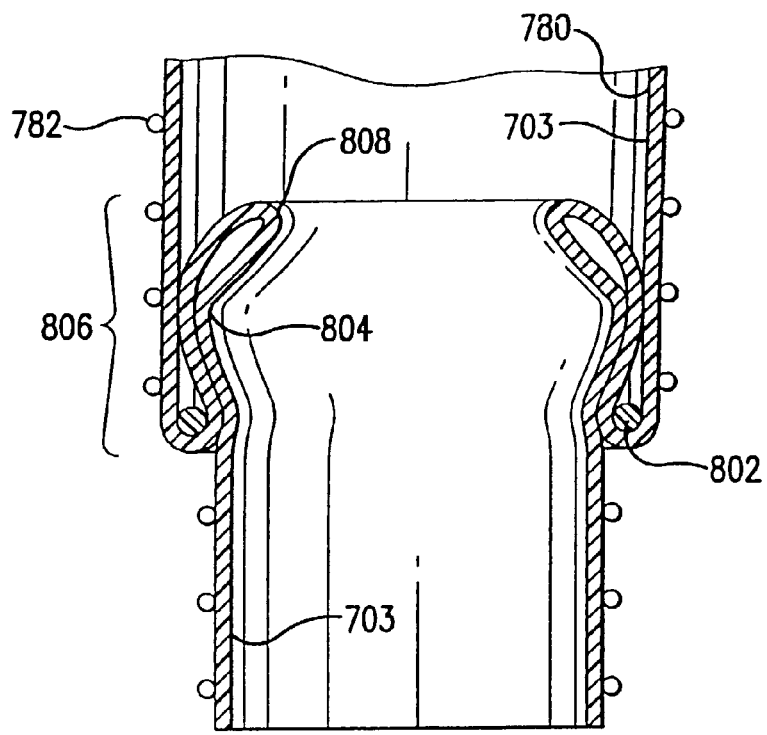
FIG. 21 and FIG. 22 are enlarged partial cross-sectional views of more alternative constructions of the receiving lumen.
Figure 22:
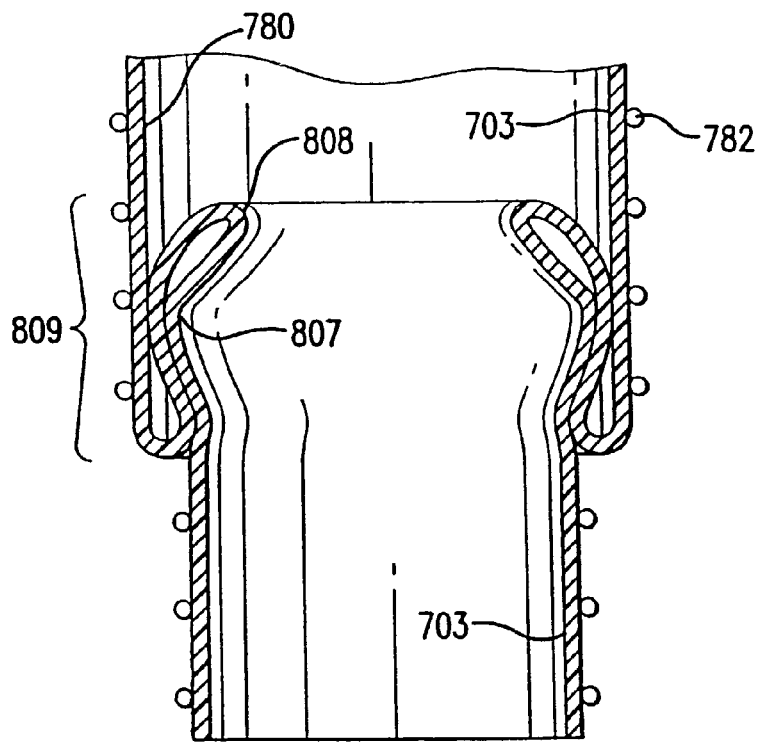
Figure 23:
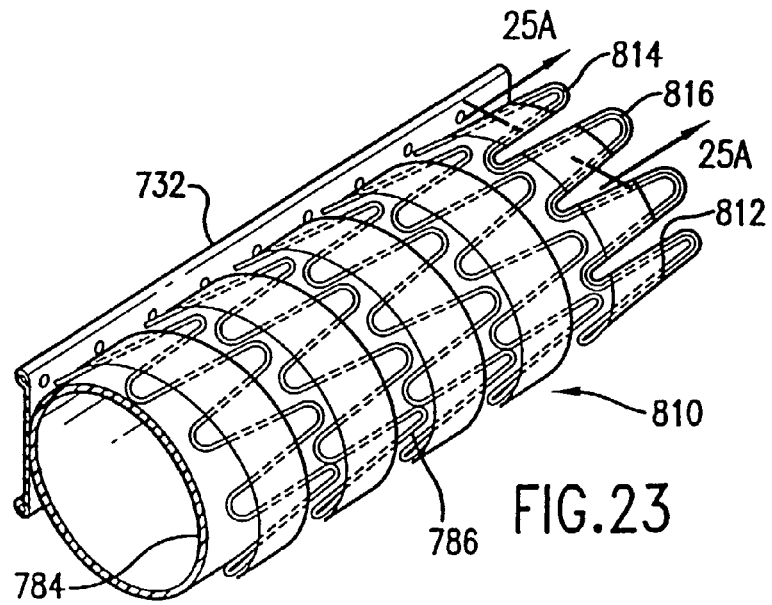
FIG. 23 is a partial perspective view of an alternate scalloped construction of the proximal region of the contralateral leg component.

Alternately, localized zones of decreased diameter may be created as shown in FIGS. 21 and 22 by folding a portion of the graft member (780) back up into the receiving lumen (703). In FIG. 21, the zone of reduced diameter (806) is formed by creating a folded flap (808) of the graft material (780) around an anchoring ring (802). The flap is heat bonded in place roughly at a location (804) as shown. In FIG. 22, the zone of reduced diameter (809) is formed of flap (808) and heat bonded roughly at a location (807) in a similar manner but without any anchoring ring. The localized interference using these methods tends to cover a larger area and the flap (808) provides a more flexible member to seal against the outside diameter of the contralateral leg component (730).

One further aspect of ensuring a good seal between the stent-graft components involves the use of a scalloped stent-graft construction at the distal end of the contralateral leg component (810). To create this scalloped construction, the graft material between the apexes of the stent member is removed on the last turn of the stent. For example scallop (812) may be formed by removing (or cutting and folding under) the graft material from between a first apex (814) and an adjacent apex (816).

Figure 24A:
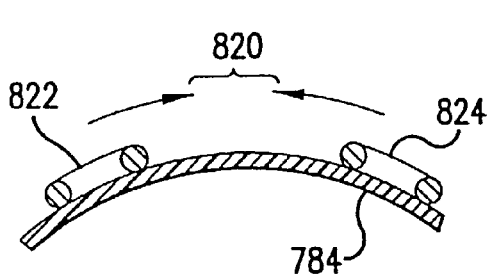
FIGS. 24A and 24B are cross-sectional views taken along section line 24A-24A as shown in FIG. 14A depicting a free state and a forced state respectively.
Figure 25A:
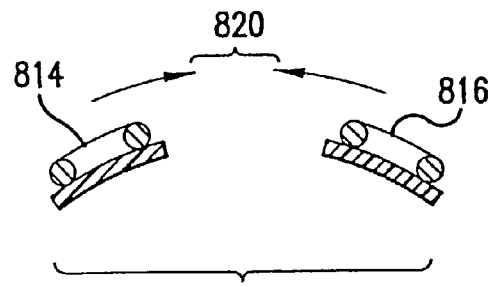
FIGS. 25A and 25B are cross-sectional views taken along section line 25A-25A as shown in FIG. 23 depicting a free state and a forced state respectively.
Figure 24B:
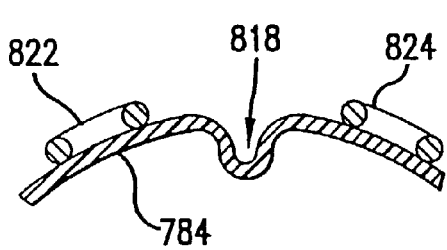
Figure 25B:
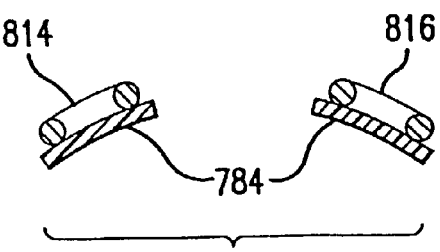

The advantage of using a scalloped arrangement are illustrated in FIGS. 24A through 25B. FIG. 24A shows a cross-section of the fully expanded contralateral leg component (730) having an unscalloped construction. A first apex (822) and an adjacent apex (824) have continuous graft material (784) in the area between them. When the apex (822) and the adjacent apex (824) are forced together in the directions of the arrows (820), the graft material (784) forms a buckle or wrinkle (818) which is a potential leak path or is a potential site for thrombogenic material to build up as seen in FIG. 24B. The scalloped construction shown in FIGS. 25A and 25B, on the other hand, have no graft material between the first apex (814) and the adjacent apex (816) and therefore when forced together do not form a graft material wrinkle.

The wrinkle (818), mentioned above may also be formed when the stent-graft is not allowed to expand to its complete diameter. For instance it is quite common that the receiving lumen or vessel wall internal diameter is smaller than the fully expanded stent-graft outer diameter. This being the case, it should be clear that the scalloped construction may alternately be used at any of the terminal openings of the main body component or the contralateral leg component. Preferably, the distal end (702) of the main body component (700) also has this scalloped construction as shown in FIGS. 14A and 14B.

Figure 27A:
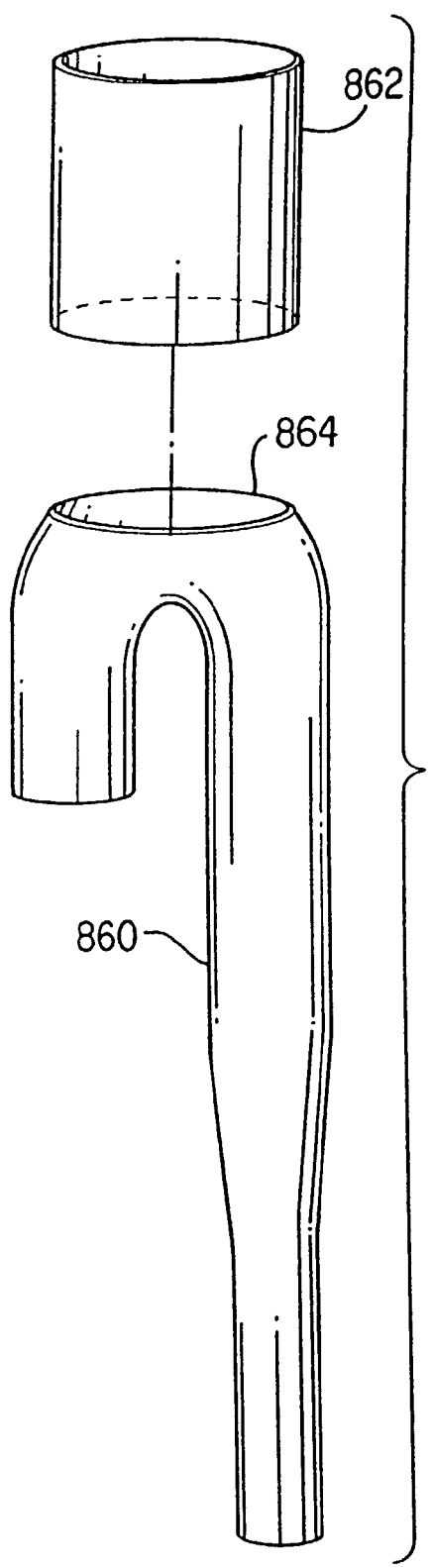
FIG. 27A is a front view of the unassembled components of an alternate construction of the graft element.
Figure 27B:
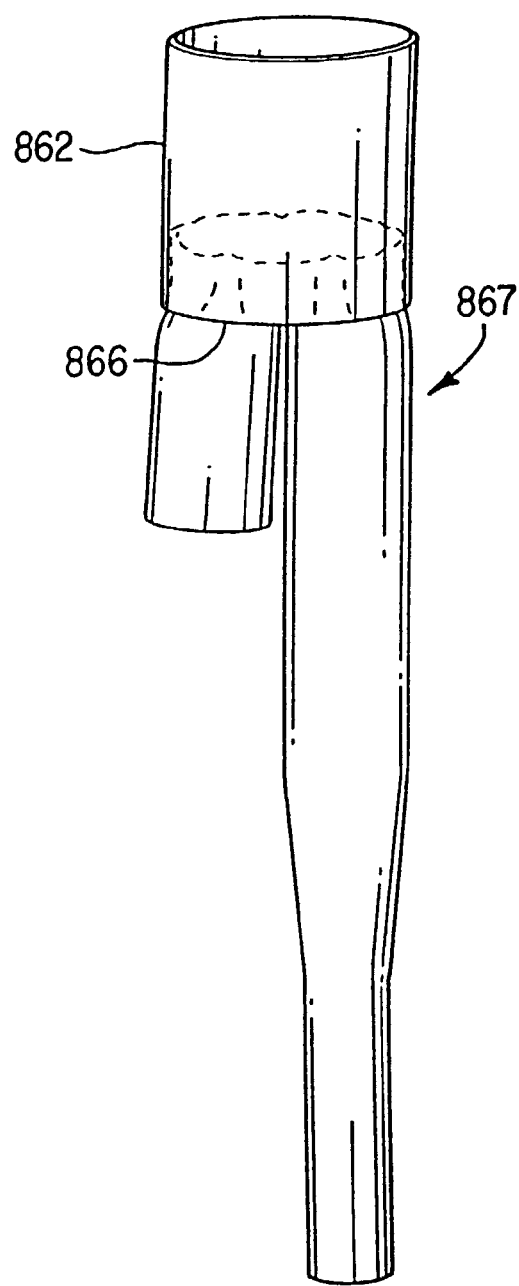
FIG. 27B is a front view of the assembled graft element according to the alternative construction of FIG. 27A.

In the previous discussion we have referred generally to a stent-graft that includes a graft member. While the construction of such straight stent grafts are discussed at length above, the construction of a bifurcated graft member is illustrated in FIGS. 26, 27A and 27B. A bifurcated graft member suitable for construction of the main body component (700) discussed above is generally formed of two graft members: the ipsilateral tapered graft (840) and the contralateral tapered graft (842). The separate contralateral leg graft component (844) is a straight or tapered section and may be formed according to the principles discussed.

The ipsilateral tapered graft (840) has three sections which are separated by tapers. A top section (846), a middle section (848), and a bottom section (850). The body component graft (854) is formed by heat bonding the top section (846) of ipsilateral tapered graft (840) to the top section (847) of contralateral tapered graft (842). This heat bonding forms a common septum (856) which in a preferred embodiment is subsequently cut away to produce a smooth bifurcation. Cutting away the septum material prevents fluid flow disturbance or blockage that could result from deviation of the septum. Such deviation is caused by the fluid pressure and is aggravated if the stent-graft is radially compressed in a manner which causes the septum to become loose or no longer taut.

In another embodiment, a graft section may be constructed in the manner illustrated in FIGS. 27A and 27B. According to this embodiment, the body component graft (867) is constructed from two pieces. A tubular graft section (860) is bent into a 'U-shape'. A top hole (864) is formed by notching the top of the 'U-shape' Upper graft section (862) is placed over the top hole (864) of tubular graft section (860). The two pieces are bonded together at the bonding interface (866). Preferably, the two graft pieces are heat bonded while supported by interior mandrels (not shown) to obtain the desired shape and smooth interior. However, upper graft section (862) may be attached to the tubular graft section (860) at the bond interface (866) in any manner that provides a sufficiently leak free seal. For example the components may be sutured together or adhesive bonded.

In use, the modular bifurcated stent-graft is typically delivered percutaneously through the vasculature of the body. Preferably the prosthesis is delivered by way of a restraining member as described in detail above. FIGS. 28A though 28E diagrammatically illustrate deployment of a bifurcated stent-graft with a restraining member (902) using a percutaneously catheter assembly. Referring to FIG. 28A, a multilumen catheter assembly (928) has been inserted to a selected site within a body lumen. The main body component (700) of a bifurcated stent-graft is held in a compressed state about a guidewire (926) and a guidewire lumen (929) by a restraining member (902) and a coupling member (906). The collapsed main body component (700) is held axially in place prior to deployment by a distal barrier (930) and a proximal barrier (932). The distal (930) and proximal (932) barriers are typically affixed to the guidewire lumen (929). The coupling member (906) extends through the eyelets (920) of the restraining member (902) forming chain knots and into the multilumen catheter (928).

FIG. 28A shows advancement of the multilumen catheter (928) with the distally located main body component (700) and the restraining member (902) into implantation position, typically at the bifurcation of a major vessel. During deployment it is critical that the surgeon align the main body component (700) so that the ipsilateral leg (726) will extend down one branch of the bifurcated vessel, and so the receiving hole (704) and the receiving lumen (703) will be lined up with the other branch of the bifurcated vessel so as to receive the contralateral leg component (730).

One way of facilitating this alignment is to provide radiopaque markers so that the surgeon may readily determine the rotational position of the main body component (700) prior to deployment or release from the restraining member (902). In a preferred embodiment, a long marker (934) is located on the contralateral side of the compressed assembly and a shorter marker (936) is placed on the ipsilateral side. Preferably these markers are placed on the stent prior to compression but may alternatively be part of the restraining member. Having one marker of a different length allows the surgeon to identify the orientation of both the ipsilateral leg and the receiving lumen relative to the bifurcated vessel.

Once the assembly is properly aligned and positioned for implantation, the coupling member (906) is pulled and the restraining member (902) begins to release the implant, typically at the distal end first. In the preferred embodiment, the restraining member (902) is located down the side as shown because it is less likely to interfere with deployment of the receiving lumen (703).

FIG. 28B shows the main body component (700) radially expanding as the coupling member (906) is retracted through the eyelets (920) of the restraining member (902) and into the catheter assembly (928). In the preferred embodiment, the restraining member (902) has been fixedly attached to the main body component (700) with a number of sutures along the length of the main body component to prevent any relative longitudinal movement between the implanted prosthesis and the restraining member (902). The restraining member may optionally employ a retracting or pull-down mechanism as described at length above.

FIG. 28C shows the main body component (700) and the restraining member (902) in final implantation position at the vessel bifurcation after the guidewire (926) and the catheter assembly (928) have been retracted.

Figure 28E:
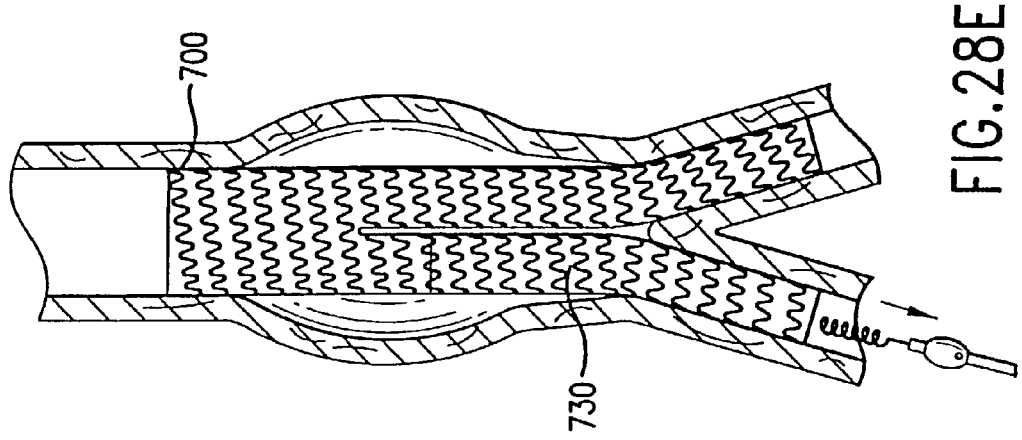
Figure 28D:
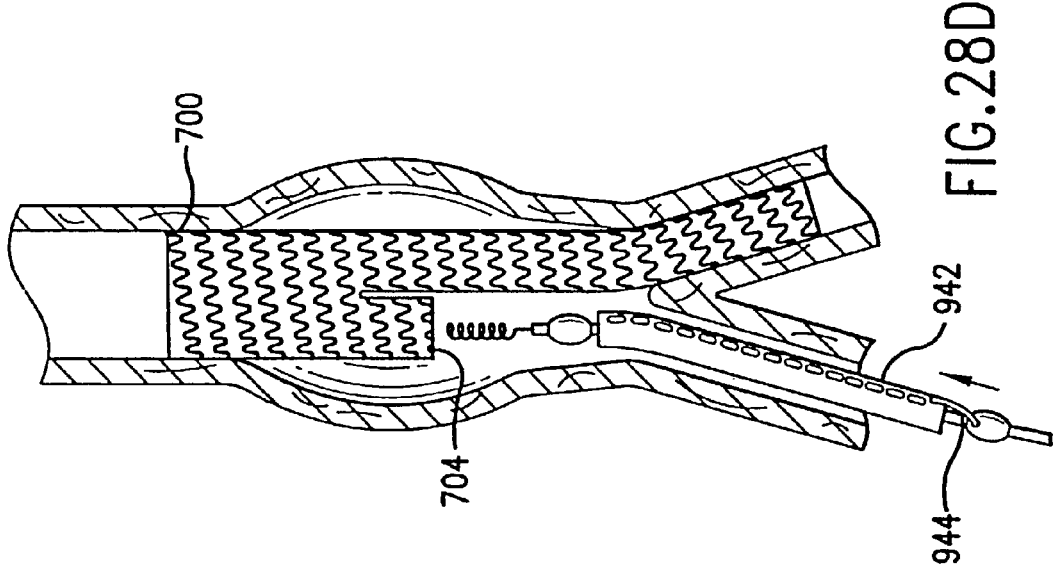
Figure 29B:
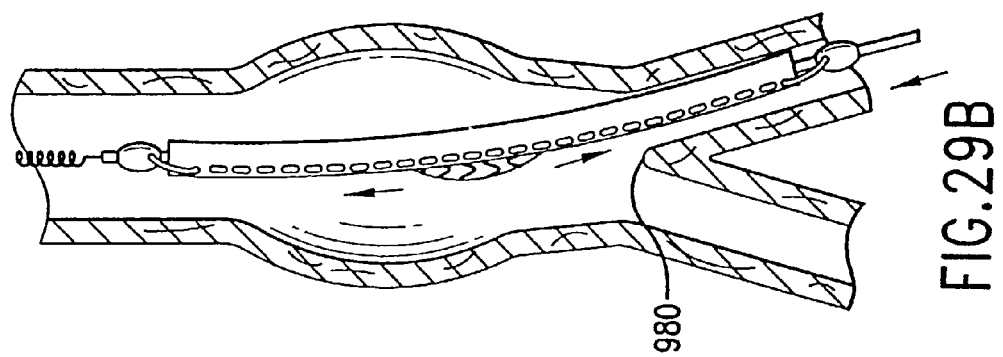
FIGS. 29A, 29B, 29C, and 29D diagrammatically show deployment of a bifurcated stent-graft using an alternate delivery system.
Figure 29A:
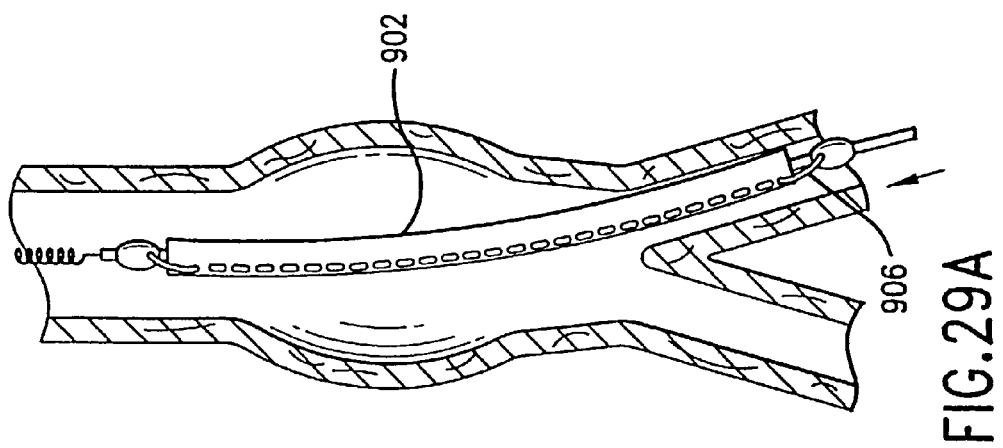
Figure 29C:
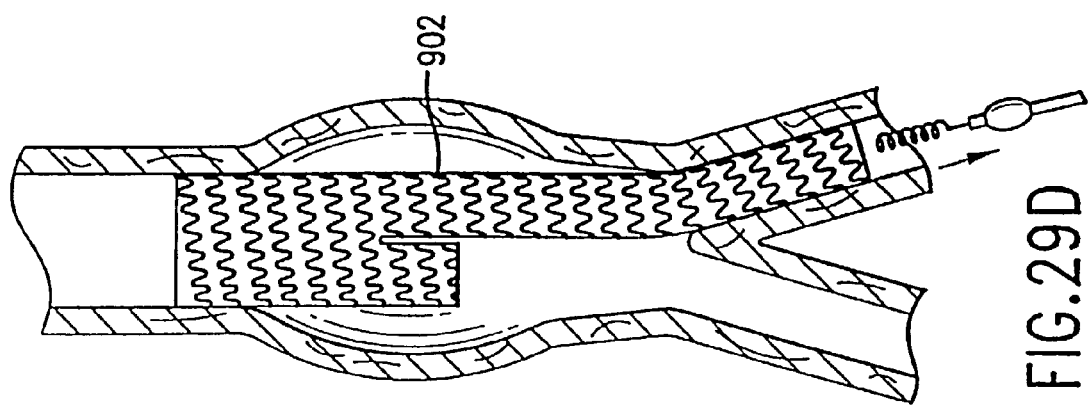
Figure 29D:
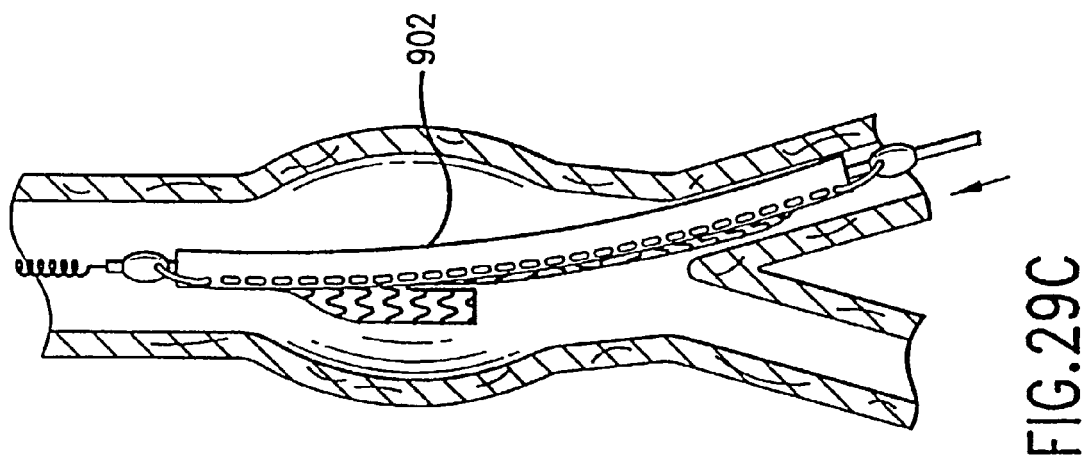

FIG. 28D shows the contralateral leg component (730) being delivered to the contralateral receiving hole using a restraining member (942). The procedure for positioning and releasing the contralateral leg component (730) is the same as that described above for implantation of a generally cylindrical stent-graft except that certain radiopaque markers may be employed to ensure its proper position relative to the bifurcation point (728) of main body component (700).

Radiopaque markers may be located, for example, to indicate the position of the receiving hole (704), the distal end (734) of the contralateral leg component (730), and the bifurcation point (728) of the main body component (700). These markers serve to indicate the position of the contralateral leg component as it enters the receiving hole (704) and its ultimate position relative to the receiving lumen (703) which begins at bifurcation point (728). In a preferred embodiment illustrated in FIG. 19, the radiopaque wires (794) may be heat bonded or imbedded into the graft material (780) around the periphery of the receiving lumen. Such radiopaque wires could be used in other places such as the contralateral leg component lumen, the ipsilateral leg lumen or the lumen at the distal end of the main body component (700).

FIG. 28E shows the assembled bifurcated stent-graft in its final implantation state with the contralateral leg component expanded into and engaged with the receiving lumen of the main body component (700).

FIGS. 29A through 29D diagrammatically show the same stent or stent-graft components being deployed except that the restraining member (902) is released from the center out towards as the coupling member (906) is retracted. This may provide more accurate placement relative to the bifurcation point of the vessel instead of relative to the distal end as with end release.

While this invention has been described with reference to illustrative embodiments, this description is not intended to be construed in a limiting sense. Various modifications and combinations of the illustrative embodiments, as well as other embodiments of the invention will be apparent to persons skilled in the art upon reference to the description. It is therefore intended that the appended claims encompass any such modifications or embodiments.

The invention claimed is:

1. An implantable endoluminal prosthesis adapted for placement within a body, comprising:
    a stent member having an outer surface when said stent member is in an expanded configuration;
    a graft member;
    a first tape member having a first width and a second tape member having a second width different from said first width;
    said first tape member covering only a portion of said outer surface of said stent member;
    said second tape member covering only a portion of said outer surface of said stent member;
    at least one of said first tape member and said second tape member being bonded to said graft member and securing the stent member and graft member together.

2. The endoluminal prosthesis of claim 1, further comprising at least a first segment and a second segment which have a different axial stiffness.

3. The endoluminal prosthesis of claim 1, in which at least one of said first tape member and said second tape member has a varying thickness along a tape member length.

4. The endoluminal prosthesis of claim 1, in which said stent member has a first stent segment and a second stent segment which have a different structural property.

5. The endoluminal prosthesis of claim 4, in which said graft member has a first graft portion and a second graft portion with a different structural property.

6. The endoluminal prosthesis of claim 1, in which said prosthesis has a first segment and a second segment which have a different flexibility.

7. The endoluminal prosthesis of claim 1, in which said prosthesis has a main body component and a contralateral leg component.

8. The endoluminal prosthesis of claim 7, in which the main body component has a higher axial stiffness than the contralateral leg component.

9. The endoluminal prosthesis of claim 7, in which the contralateral leg component has a greater flexibility than the main body component.

10. An endoluminal prosthesis, comprising:
a stent member having an outer surface when said stent member is in an expanded configuration;
a graft member having a generally tubular shape when said endoluminal prosthesis is in said expanded configuration;
said stent member and said graft member generally coaxial to one another when said stent is in said extended configuration;
a first tape member having a first width and a second tape member having a second width different from said first width;
said first tape member helically configured about an axial length of said graft member when said graft member is in said expanded configuration, and said first tape member covering a portion of said outer surface of said stent member and securing said stent member and said graft member together;
said second tape member covering a portion of said outer surface of said stent member.

11. The endoluminal prosthesis of claim 10, further comprising a first segment having said first tape member and a first axial stiffness and a second segment having said second tape member and a second axial stiffness which is different from said first axial stiffness.

12. The endoluminal prosthesis of claim 10, in which at least one of said first tape member and said second tape member has a varying thickness.

13. The endoluminal prosthesis of claim 10, in which said stent member has a first stent portion with a structural property different from a second stent portion.

14. The endoluminal prosthesis of claim 13, in which said graft member has a first graft portion with a structural property different from a second graft portion.

15. The endoluminal prosthesis of claim 10, further comprising a first segment having said first tape member and a first flexibility and a second segment having said second tape member and a second flexibility which is different from said first flexibility.

16. The endoluminal prosthesis of claim 10, in which said prosthesis has a main body component and a contralateral leg component.

17. The endoluminal prosthesis of claim 16, in which the main body component has a higher axial stiffness than the contralateral leg component.

18. The endoluminal prosthesis of claim 16, in which the contralateral leg component has a greater flexibility than the main body component.

19. The endoluminal prosthesis of claim 10, in which said first tape member and said second tape member are each bonded to said graft member.

20. An implantable endoluminal prosthesis adapted for placement within a body, comprising:
a stent member having a first stent member segment with a outer surface and a second stent member segment having a outer surface;
a graft member having a first graft member portion and a second graft member portion;
said first tape member having a first width and covering only a portion of said outer surface of said first stent member segment, said first tape member being bonded to said first graft member portion and securing the first stent member segment and said first graft member portion together;
said second tape member having a second width and covering only a portion of said outer surface of said second stent member segment, said second tape member being bonded to said second graft member portion and securing the second stent member segment and said second graft member portion together;
said second width different from said first width.

21. An implantable endoluminal prosthesis adapted for placement within a body, comprising:
a stent member having an expandable and expanded configuration, said stent member having an outer surface when in said expanded configuration;
a graft member;
said stent member comprising a first stent segment and a second stent segment;
a first tape member having a first width and covering a portion of an outer surface of said first stent segment and securing the first stent segment and the graft member together;
a second tape member having a second width and covering a portion of an outer surface of said second stent segment;
said outer surface of said stent member comprising a portion free of cover by said first tape member;
said second width different from said first width.

* * * * *